(12) United States Patent
Che et al.

(10) Patent No.: US 8,877,353 B2
(45) Date of Patent: Nov. 4, 2014

(54) PLATINUM (II) TETRADENTATE ONCN COMPLEXES FOR ORGANIC LIGHT-EMITTING DIODE APPLICATIONS

(75) Inventors: Chi Ming Che, Hong Kong (HK); Chi Fai Kui, Hong Kong (HK); Chi Chung Kwok, Hong Kong (HK)

(73) Assignee: Versitech Limited, Hong Kong (HK)

( * ) Notice: Subject to any disclaimer, the term of this patent is extended or adjusted under 35 U.S.C. 154(b) by 658 days.

(21) Appl. No.: 13/181,936

(22) Filed: Jul. 13, 2011

(65) Prior Publication Data

US 2012/0018711 A1 Jan. 26, 2012

Related U.S. Application Data

(60) Provisional application No. 61/366,359, filed on Jul. 21, 2010.

(51) Int. Cl.
| | | |
|---|---|---|
| H01L 51/54 | (2006.01) | |
| C07F 15/00 | (2006.01) | |
| C07D 213/30 | (2006.01) | |
| H01L 51/00 | (2006.01) | |
| H01L 51/50 | (2006.01) | |

(52) U.S. Cl.
CPC ......... *H01L 51/0087* (2013.01); *C07D 213/30* (2013.01); *H01L 51/5036* (2013.01); *H01L 51/5016* (2013.01); *Y10S 428/917* (2013.01)
USPC .......... 428/690; 428/917; 313/504; 313/506; 257/40; 546/6; 244/225

(58) Field of Classification Search
CPC .............. C07D 213/30; H01L 51/0087; H01L 51/5036; H01L 51/5016
See application file for complete search history.

(56) References Cited

U.S. PATENT DOCUMENTS

| | | | |
|---|---|---|---|
| 3,172,862 A | 3/1965 | Gurnee et al. | |
| 4,356,429 A | 10/1982 | Tang | |
| 6,653,654 B1 | 11/2003 | Che | |
| 7,361,415 B2 | 4/2008 | Che et al. | |
| 7,655,323 B2 * | 2/2010 | Walters et al. | 428/690 |
| 7,691,495 B2 | 4/2010 | Che et al. | |
| 2007/0082284 A1 * | 4/2007 | Stoessel et al. | 430/84 |
| 2012/0223634 A1 * | 9/2012 | Xia et al. | 313/504 |
| 2013/0082245 A1 * | 4/2013 | Kottas et al. | 257/40 |

OTHER PUBLICATIONS

Siu et al., Chemical Communications, (2005), Issue (8), pp. 1025-1027.*

Kondakova, Marina E., et al., "High-efficiency, low-voltage phosphorescent organic light-emitting diode devices with mixed host", Journal of Applied Physics, 104, 094501, 2008, pp. 094501-1-094501-17.

Mehta, Dalip Singh, et al., "Light out-coupling strategies in organic light emitting devices", Proc. of ASID'06, Oct. 8-12, New Delhi, pp. 198-201.

Chu, Ta-Ya, et al., "Highly efficeint and stable inverted bottom-emission organic light emitting devices", Applied Physics Letters, 89, 053503, 2006, pp. 053503-1-053503-3.

* cited by examiner

*Primary Examiner* — Dawn L. Garrett

(74) *Attorney, Agent, or Firm* — Amin, Turocy & Watson, LLP

(57) ABSTRACT

Described are novel platinum (II) containing organometallic materials. These materials show green to orange emissions with high emission quantum efficiencies. Using the materials as emitting materials; pure green emitting organic light-emitting diodes can be fabricated. Since the novel platinum (II) containing organometallic materials are soluble in common solvents, solution process methods such as spin coating and printing can be used for device fabrication.

20 Claims, 2 Drawing Sheets

PLATINUM (II) TETRADENTATE ONCN COMPLEXES FOR ORGANIC LIGHT-EMITTING DIODE APPLICATIONS

CROSS-REFERENCE TO RELATED APPLICATIONS

This application claims priority to provisional application Ser. No. 61/366,359, filed on Jul. 21, 2010, which is incorporated herein by reference.

TECHNICAL FIELD

Described are a class of new organometallic materials and their usage in organic light-emitting diode (OLED) and polymer light emitting diode (PLED). The organometallic materials show good emission quantum efficiency and soluble in common organic solvents. Making use these materials, high efficiency single color and white OLED (WOLED) can be fabricated by various techniques including vacuum deposition, spin coating or printing methods.

BACKGROUND

In 1965 Edward F. Gurnee and Fernandez Reet Teoste first observed and studied organic electroluminescence (U.S. Pat. No. 3,172,862). Later on, Tang in Eastman Kodak disclosed double-layer structure OLED (organic light emitting diode, U.S. Pat. No. 4,356,429; Appl. Phys. Lett. 1987, 51, 12, 913). This diode was based on employing a multilayer structure including an emissive electron-transporting layer (fabricated from $Alq_3$ (q=deprotonated 8-hydroxyquinolinyl)) and a hole-transport layer of suitable organic materials. Afterward, research on materials used in OLED becomes a hot research topic. OLED possesses many advantages such as: low operating voltage; ultra thin; self emitting; good device efficiency; high contrast and high resolution which suggest the possible use of OLED in flat panel displays and lighting.

There are two classes of emitting materials for OLED application: fluorescent and phosphorescent materials. Phosphorescent materials become the major trend for emitting materials development since 75% excitons produced from OLED are in triplet, only 25% excitons are in singlet. It means the maximum device efficiency for phosphorescent materials are 3 times higher than fluorescent materials.

Platinum is one of the transition metals from emissive complexes with organic ligands, which have high emission quantum efficiency and good thermal stability. With these advantages, platinum(II) complexes were used as emitting materials in high performance OELDs. (Applied Physics Letters (2007), 91(6) 063508; Chemistry—A European Journal (2010), 16(1), 233-247) Among the platinum complexes used in OLED applications, pure green emitting materials with stable chemical structure are rare.

For the stability of the platinum(II) complexes, the binding energy between the ligand and platinum(II) center gets higher when the number of coordination positions in the ligand increases; that is, the binding energy between the ligand and platinum(II) center is the highest in tetradentate ligand platinum(II) complexes. Moreover, the addition of extra atom(s) between the aromatic coordination position to break the conjugation of the ligand may weaken the stability of the ligand and eventually weaken the stability of the complexes. Green emitting platinum(II) materials with bidentate ligands, tridentate ligand or tetradentate ligand with extra atom(s) between the aromatic coordination position to break the conjugation is not as good as a conjugated tetradentate ligand system.

However, most of the conjugated tetradentate ligand systems are not able to have pure green emitting materials due to their intrinsic properties such as the band gaps are limited by the MLCT transitions and the emission spectra are vibronically structured. (see U.S. Pat. No. 6,653,654; U.S. Pat. No. 7,361,415; U.S. Pat. No. 7,691,495). For these reasons, stable green emitting platinum(II) material is difficult to develop.

SUMMARY

Despite the above-mentioned problems, described herein are new platinum(II) complex systems, which have stable chemical structure, high emission quantum efficiency and pure green emission which are used as green emitting material in OLED. By changing the substitutes in the tetradentate ligand, the emission color of the platinum can also tune back to yellow or orange color. Making use of the yellow or orange emitting materials in the series, white OLED (WOLED) can also be fabricated by complementary colors mixing approach. Besides, as some of the complexes show strong excimer emission, single emitting component WOLED can be fabricated from these complexes by combining the monomer and excimer emission of one complex.

Since most of the platinum(II) complexes used for OLED application are only slightly soluble in common solvent, solution process methods such as spin coating and printing (including inkjet printing, roll to roll printing, etc.) cannot be applied. Materials described herein overcome this drawback, as all of the platinum(II) complexes described herein are soluble in common solvents, solution process methods can be applied for low cost and large area fabrication.

This invention concerns platinum(II) based emitting materials having chemical structure of structure I, their preparation and application in organic light-emitting diode (OLED) and polymer light-emitting diode (PLED).

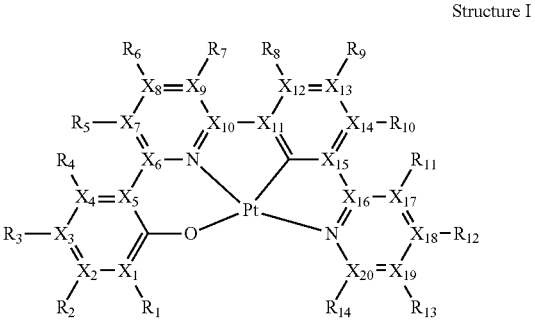

Structure I wherein $R_1$-$R_{14}$ are independently hydrogen, halogen, hydroxyl, an unsubstituted alkyl, a substituted alkyl, cycloalkyl, an unsubstituted aryl, a substituted aryl, acyl, alkoxy, acyloxy, amino, nitro, acylamino, aralkyl, cyano, carboxyl, thio, styryl, aminocarbonyl, carbamoyl, aryloxycarbonyl, phenoxycarbonyl, or an alkoxycarbonyl group. Each $R_1$-$R_{14}$ can independently form 5-8 member ring(s) with adjacent R group(s). $X_1$-$X_{20}$ are independently boron, carbon, nitrogen, oxygen, or silicon.

DETAILED DESCRIPTION

The organometallic complexes with chemical structure of Structure I are referred to cyclometallated complexes. The platinum center in Structure I is in the +2 oxidation state and has a square planar geometry.

The coordination sites of the platinum center are occupied by a tetradentate ligand. The tetradentate ligand coordinates to the platinum center through a metal-oxygen bond, a nitrogen donor bond, a metal-carbon bond and a nitrogen donor bond in a sequence of O, N, C, N (ONCN ligand). The metal-oxygen bond is a bond between deprotonated phenol or substituted phenol and platinum, the nitrogen donors are from an N-heterocyclic group such as pyridine and/or isoquinoline groups, and the metal-carbon bond is formed by benzene or substituted benzene and platinum. The chemical structure of the tetradentate ligands in current invention can be represented by Structure II:

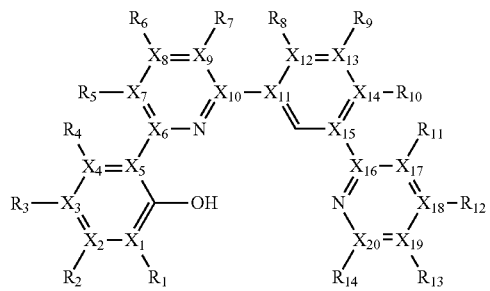

Structure II wherein $R_1$-$R_{14}$ are independently hydrogen, halogen, hydroxyl, an unsubstituted alkyl, a substituted alkyl, cycloalkyl, an unsubstituted aryl, a substituted aryl, acyl, alkoxy, acyloxy, amino, nitro, acylamino, aralkyl, cyano, carboxyl, thio, styryl, aminocarbonyl, carbamoyl, aryloxycarbonyl, phenoxycarbonyl, or an alkoxycarbonyl group. Each $R_1$-$R_{14}$ can independently form 5-8 member ring(s) with adjacent R group(s). $X_1$-$X_{20}$ are independently boron, carbon, nitrogen, oxygen, or silicon.

In one embodiment, in both Structure I and II, each $R_1$-$R_{14}$ is independently hydrogen, halogen (such as fluorine, chlorine bromine, and iodine), hydroxyl, an unsubstituted alkyl containing from 1 to 10 carbon atoms, a substituted alkyl containing from 1 to 20 carbon atoms, cycloalkyl containing from 1 to 20 carbon atoms, an unsubstituted aryl containing from 1 to 20 carbon atoms, a substituted aryl containing from 1 to 20 carbon atoms, acyl containing from 1 to 20 carbon atoms, alkoxy containing from 1 to 20 carbon atoms, acyloxy containing from 1 to 20 carbon atoms, amino, nitro, acylamino containing from 1 to 20 carbon atoms, aralkyl containing from 1 to 20 carbon atoms, cyano, carboxyl containing from 1 to 20 carbon atoms, thio, styryl, aminocarbonyl containing from 1 to 20 carbon atoms, carbamoyl containing from 1 to 20 carbon atoms, aryloxycarbonyl containing from 1 to 20 carbon atoms, phenoxycarbonyl containing from 1 to 20 carbon atoms, or an alkoxycarbonyl group containing from 1 to 20 carbon atoms.

In another embodiment, the total number of carbon atoms provided by the $R_1$-$R_{14}$ groups is from 1 to 40. In another embodiment, the total number of carbon atoms provided by the $R_1$-$R_{14}$ groups is from 2 to 30.

Figure 1:
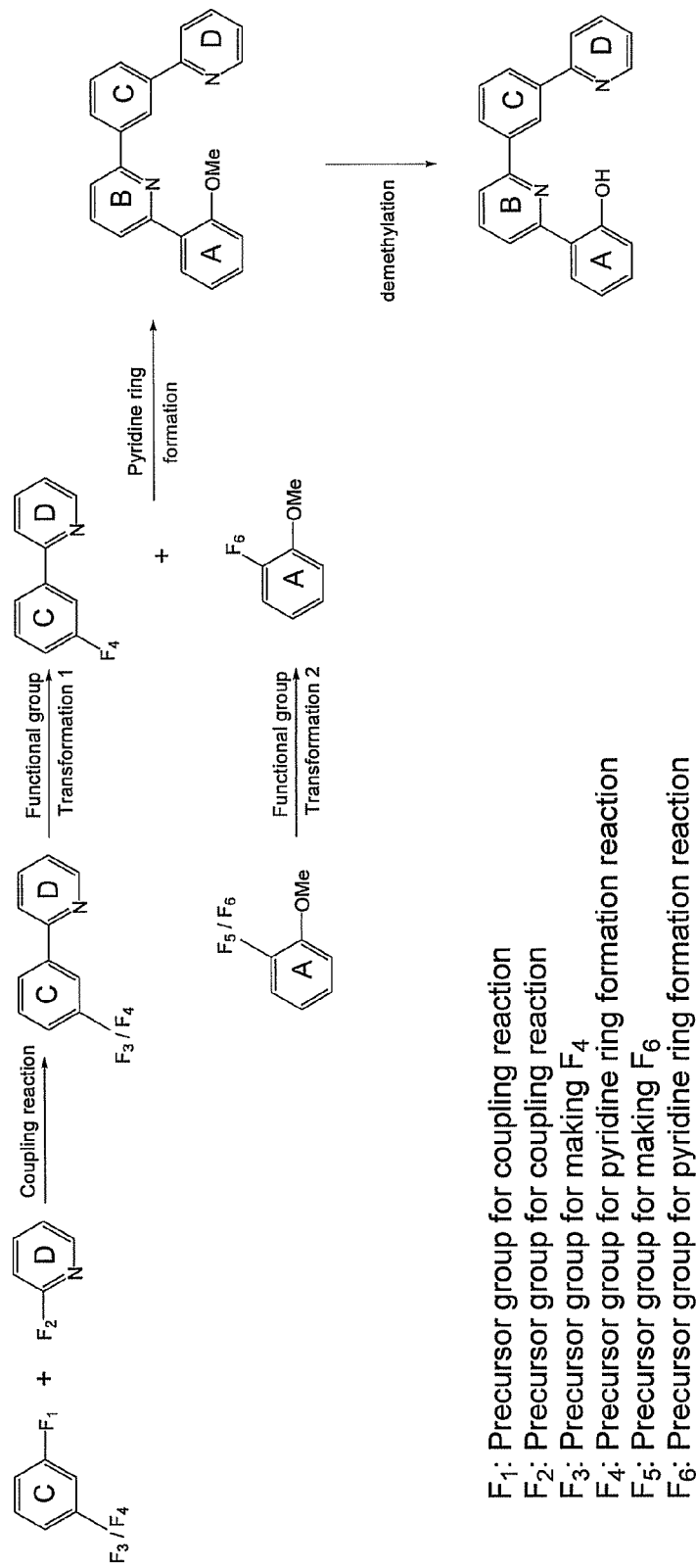
FIG. 1: Synthetic scheme for ligand with structure II.

The tetradentate ligand can be prepared by a series of reactions depicted in FIG. 1. For brevity and simplicity, aromatic ring systems A, B, C, and D as shown are unsubstituted (that is, $R_1$-$R_{14}$ as shown are hydrogen). However, although not shown in FIG. 1, but as indicated in Structures I and II, $R_1$-$R_{14}$ can be other than hydrogen.

Aromatic system C, which contains a precursor group for coupling reaction ($F_1$) and a precursor group for pyridine ring formation reaction ($F_4$) or a precursor group for making $F_4$($F_3$), is coupled with a nitrogen containing heterocyclic aromatic system D, which contains a precursor group for pyridine ring formation reaction ($F_2$), through metal coupling. If the aromatic system C contains $F_3$, it will then be transformed to $F_4$ by functional group transformation reaction. The resultant products are then reacted with aromatic system A, which can contain a methoxy group and a precursor group for pyridine ring formation ($F_6$) by pyridine ring formation reaction. (If aromatic system A with $F_6$ is not commercially available, a functional group transformation reaction can be performed to transform the precursor group for making $F_5$($F_6$) to $F_6$.) Finally, the methoxy group is transformed to hydroxyl group by demethylation reaction.

Specific examples of the ONCN ligand are shown but not restricted to below:

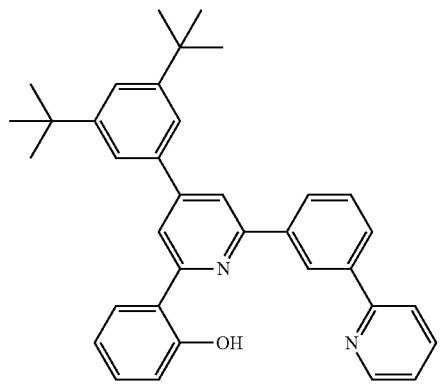

Ligand 201

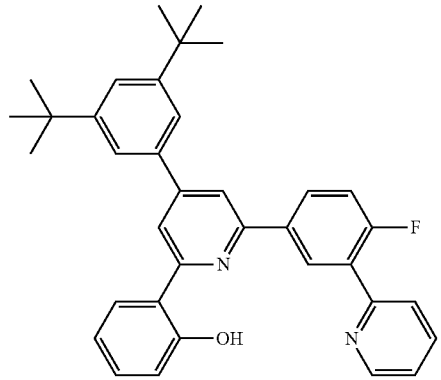

Ligand 202

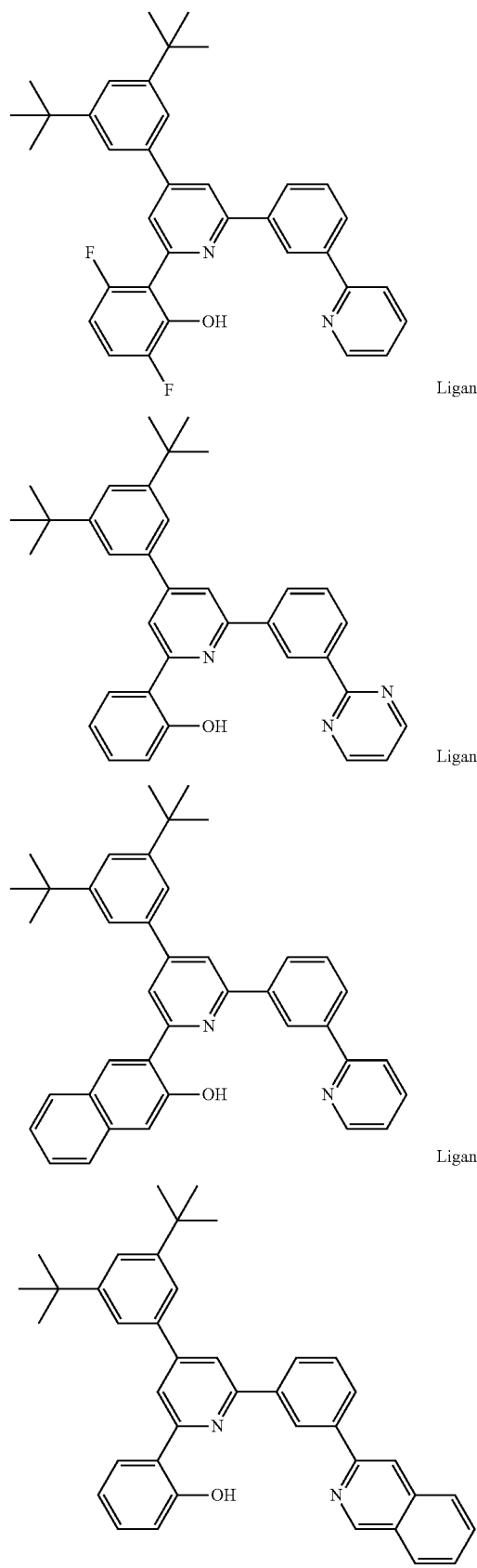
Ligand 203
Ligand 204
Ligand 205
Ligand 206
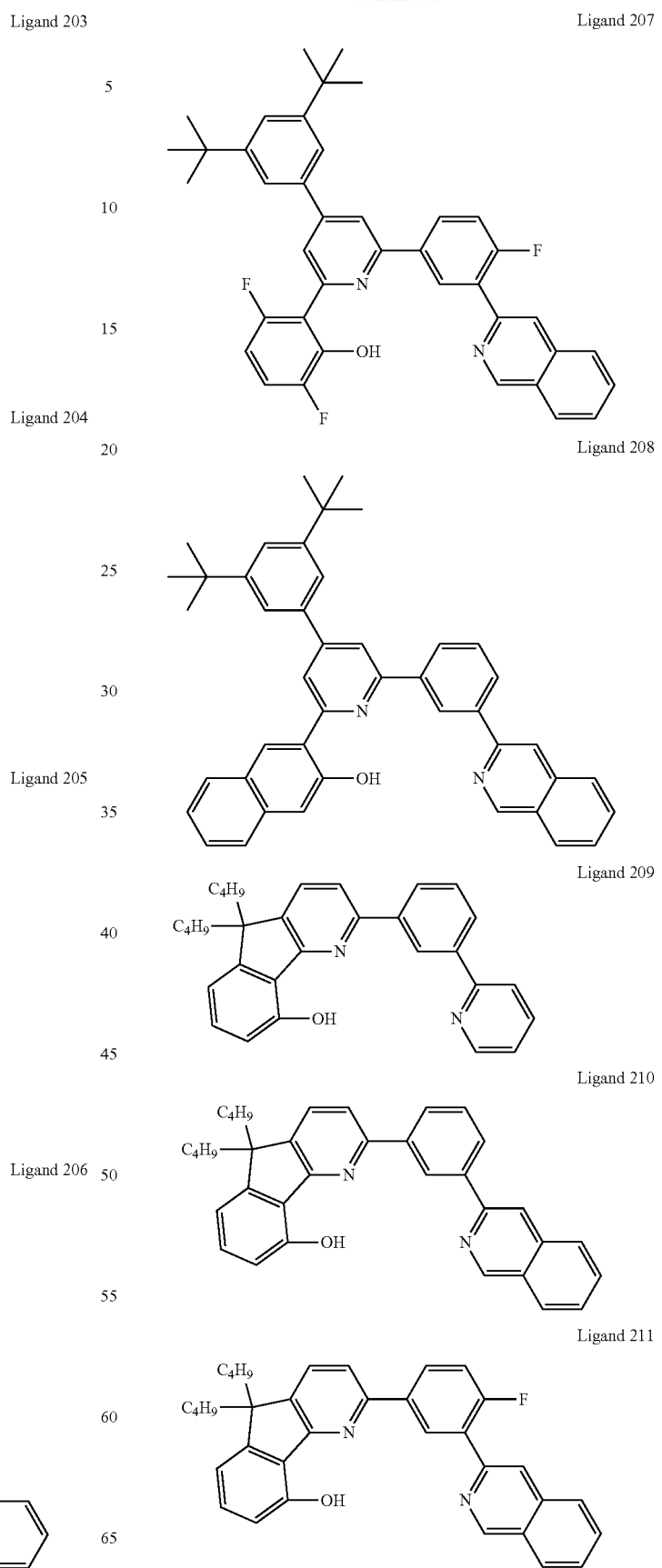
Ligand 207
Ligand 208
Ligand 209
Ligand 210
Ligand 211

Ligand 212
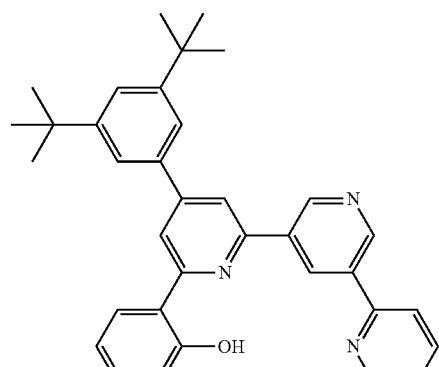
Ligand 213
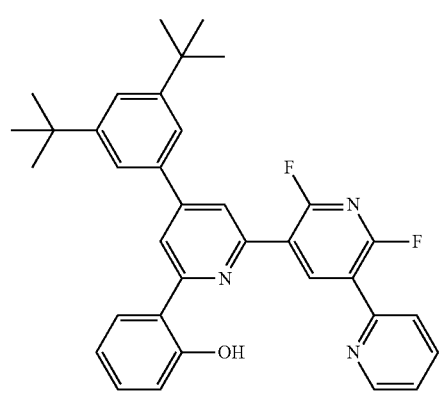
Ligand 214
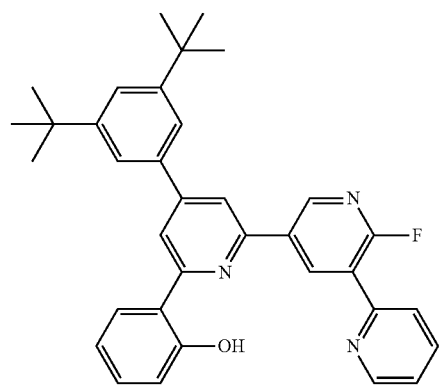
Ligand 215
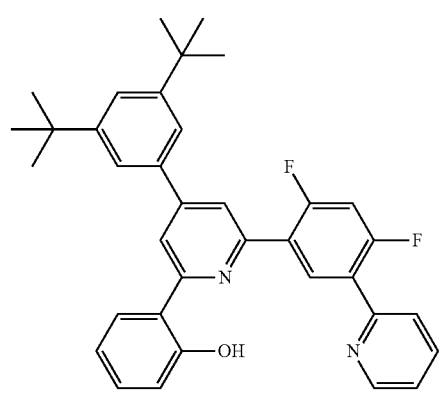
Ligand 216
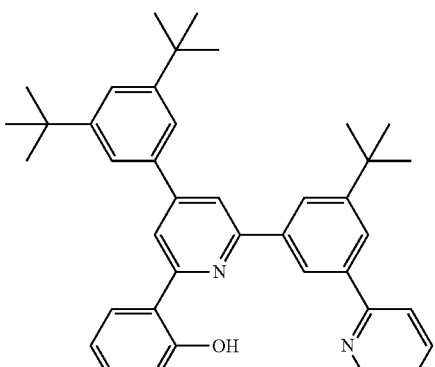
Ligand 217
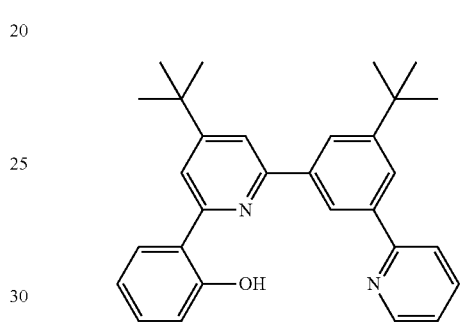
Ligand 218
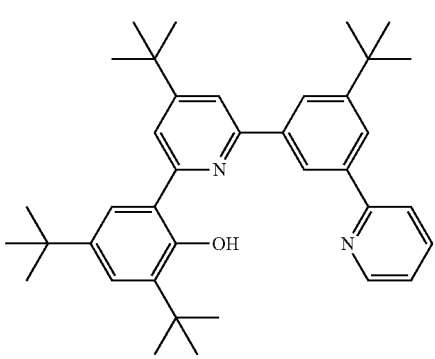
Ligand 219
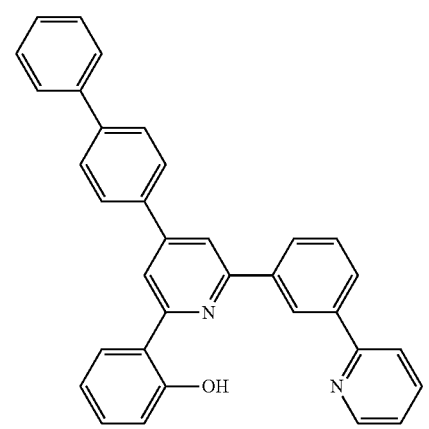

Ligand 220
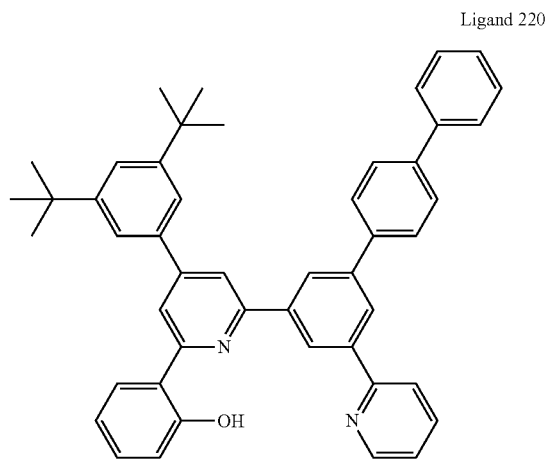

Ligand 221
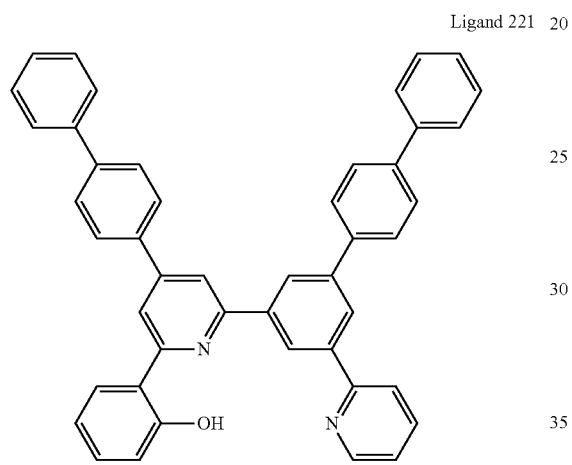

Ligand 222
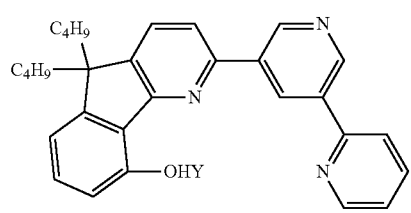

Ligand 223
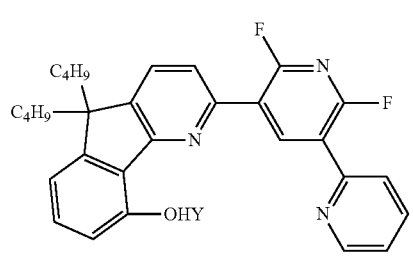

Ligand 224
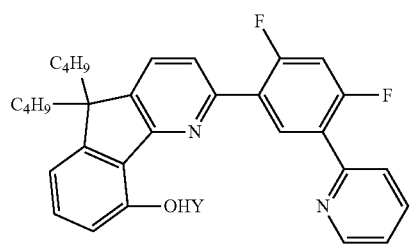

Ligand 225
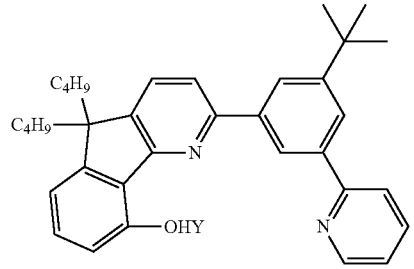

Ligand 226
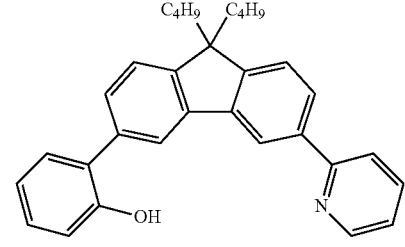

Ligand 227
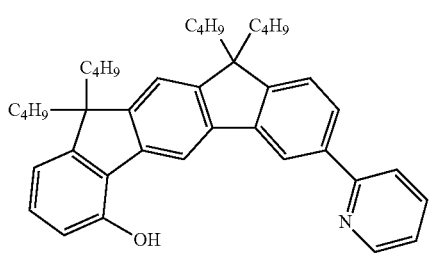

Figure 2:
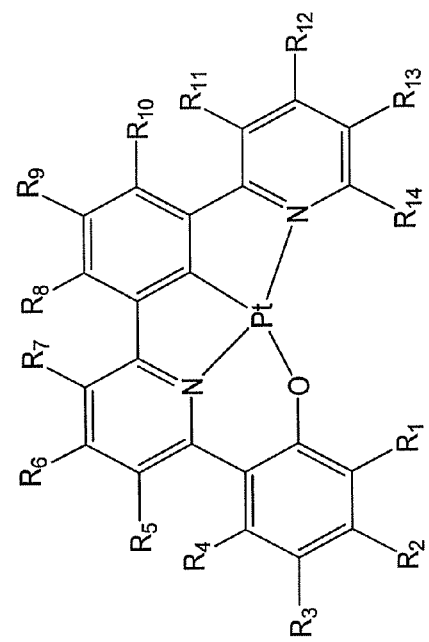
FIG. 2: Synthetic scheme for ligand with structure I.
Figure 2:
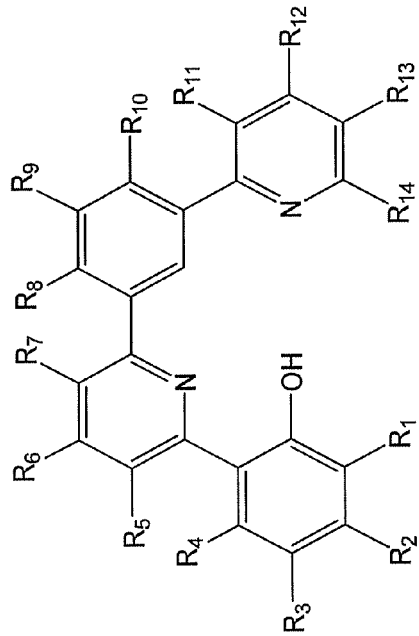

The platinum(II) complexes in current invention (represented by Structure I) can be prepared a series of reactions depicted in FIG. 2.

A ligand with structure II is reacted with a platinum compound, such as potassium tetrachloroplatinate, in a suitable solvent(s) (such as acetic acid or mixture of acetic acid and chloroform) at a suitable temperature (such as refluxing acetic acid). Platinum compounds include platinum salts, especially those containing platinum(II).

Specific examples of the platinum(II) complexes are shown but not restricted to below:

Complex 101
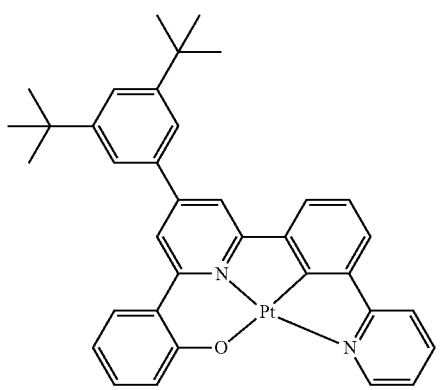

Complex 102
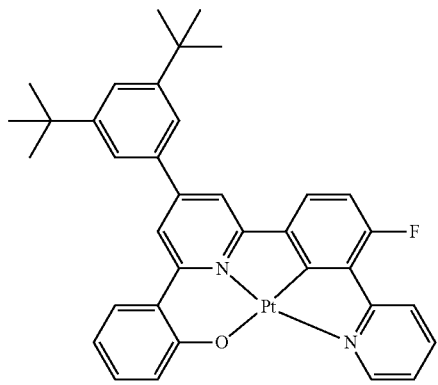
Complex 103
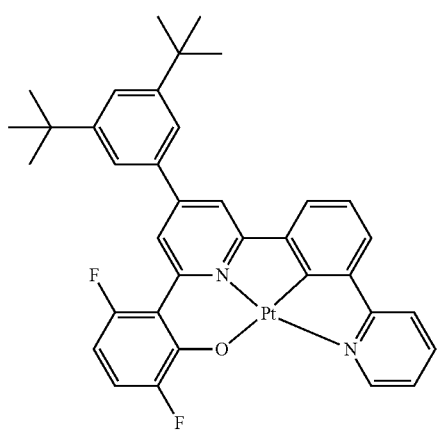
Complex 104
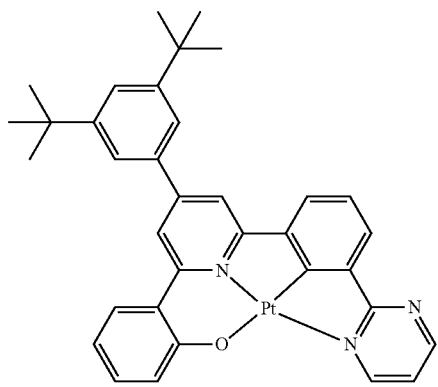
Complex 105
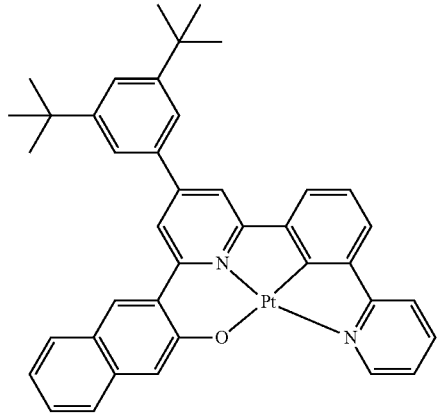
Complex 106
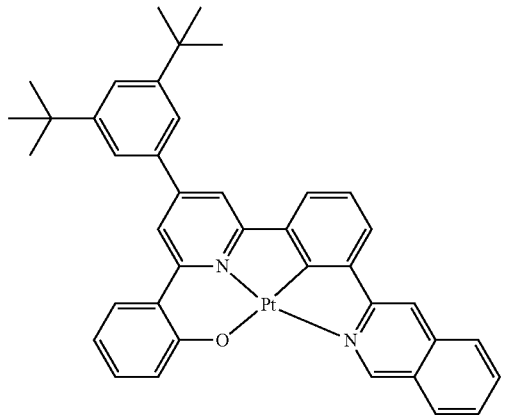
Complex 107
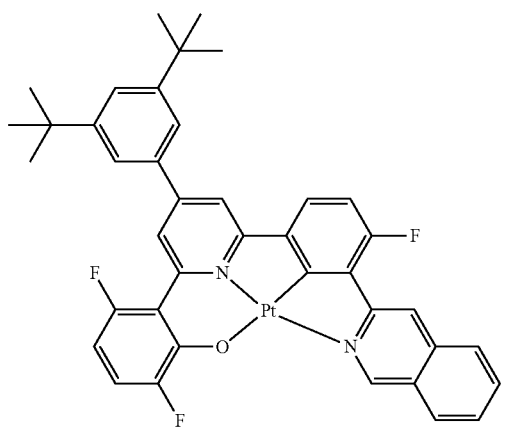
Complex 108
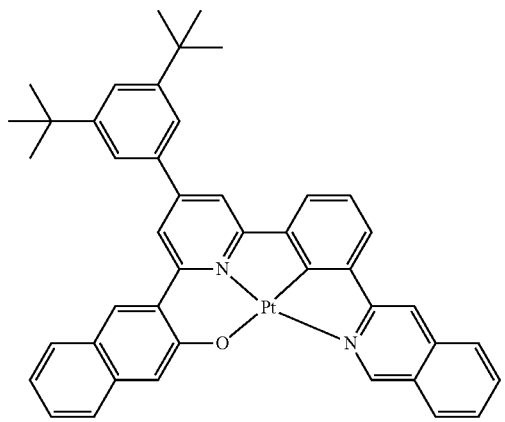
Complex 109

Complex 110
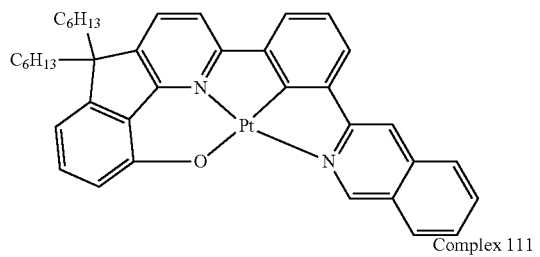
Complex 111
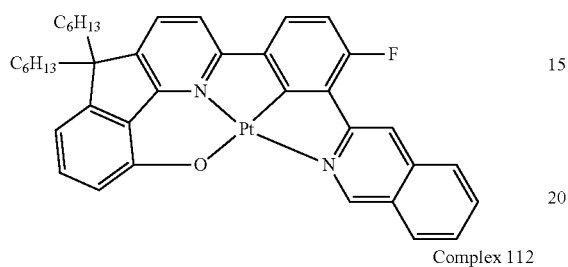
Complex 112
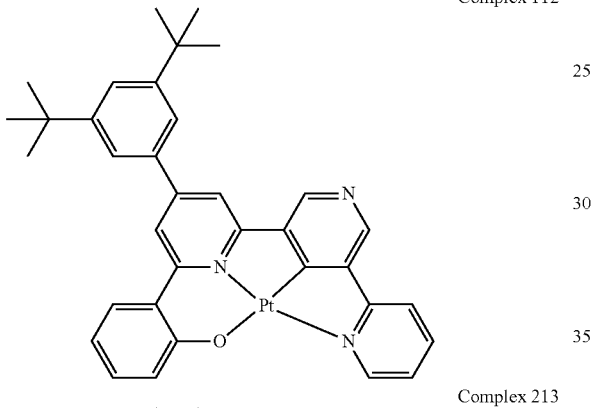
Complex 213
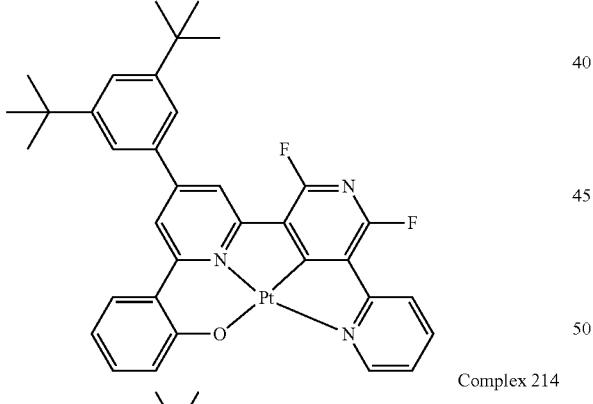
Complex 214
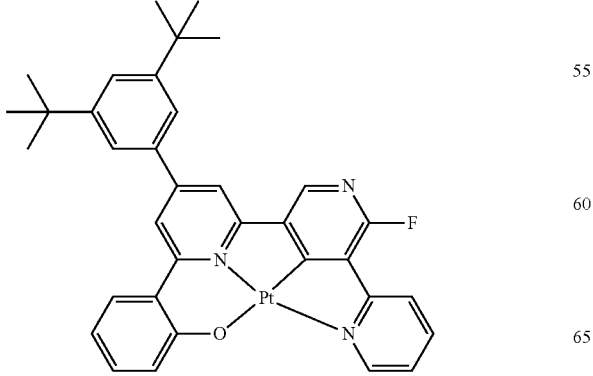
Complex 215
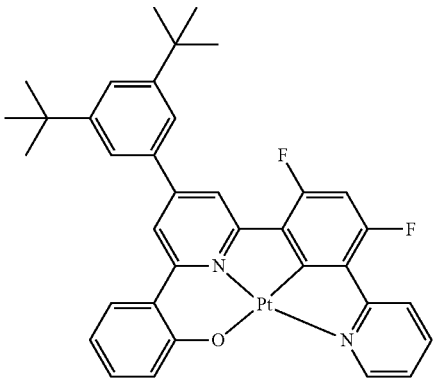
Complex 216
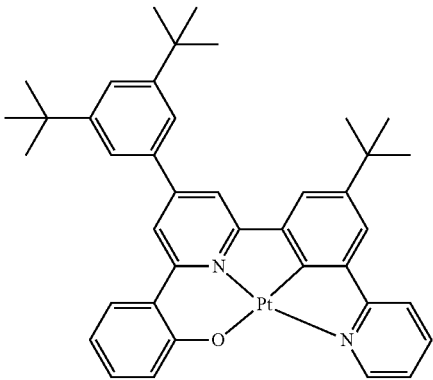
Complex 217
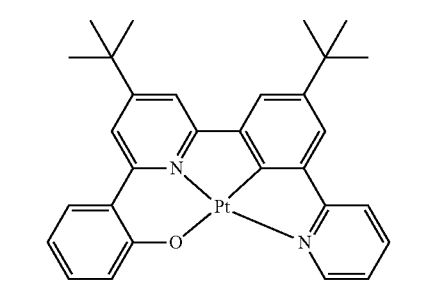
Complex 218
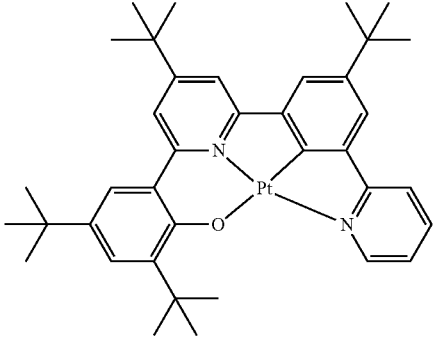

Complex 219
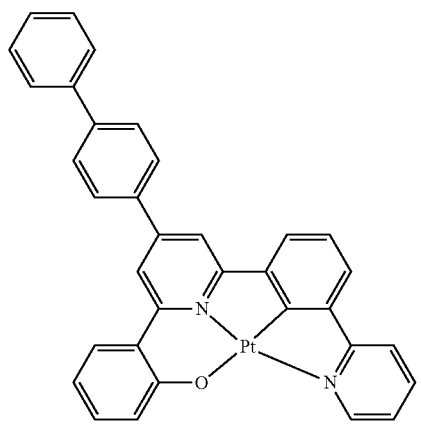

Complex 220
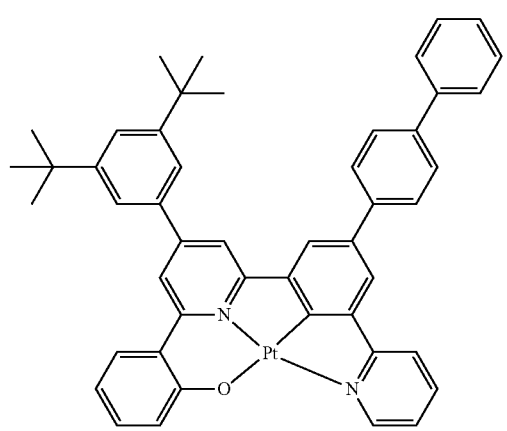

Complex 221
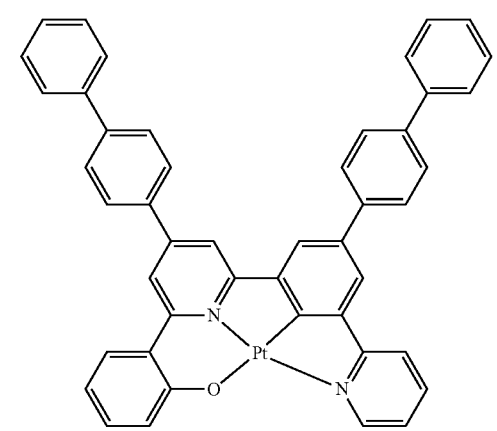

Complex 222
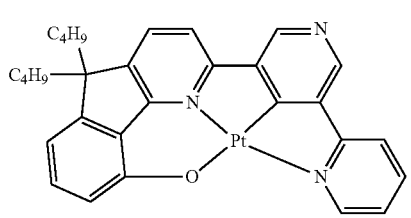

Complex 223
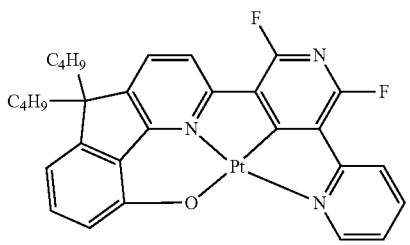

Complex 224
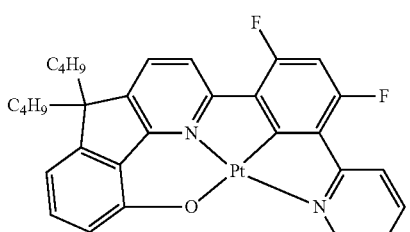

Complex 225
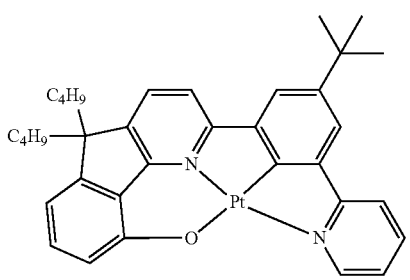

Complex 226
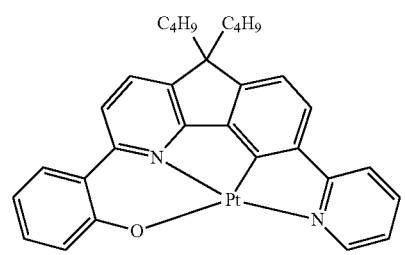

Complex 227
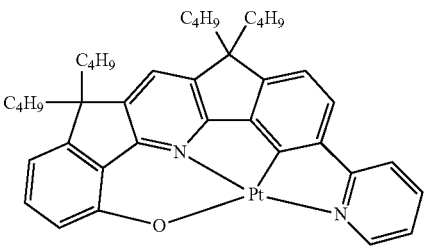

Making use of the complexes with Structure I, thermal deposition and solution process OLED can be fabricated. Below are examples for the preparation, physical properties and electroluminescent data for the platinum(II) complexes as described herein. The examples are set forth to aid in an understanding of the invention but are not intended to, and should not be interpreted to, limit in any way the invention as set forth in the claims which follow thereafter.

Unless otherwise indicated in the following examples and elsewhere in the specification and claims, all parts and percentages are by weight, all temperatures are in degrees Centigrade, and pressure is at or near atmospheric pressure.

Other than in the operating examples, or where otherwise indicated, all numbers, values and/or expressions referring to quantities of ingredients, reaction conditions, etc., used in the specification and claims are to be understood as modified in all instances by the term "about."

With respect to any figure or numerical range for a given characteristic, a figure or a parameter from one range may be combined with another figure or a parameter from a different range for the same characteristic to generate a numerical range.

Example 401

General preparation method for ligand with chemical structure of Structure II: Refer to FIG. 1, aromatic system C, which contains a precursor group for coupling reaction ($F_1$) and a precursor group for pyridine ring formation reaction ($F_4$) or a precursor group for making $F_4(F_3)$, is coupled with a nitrogen containing heterocyclic aromatic system D, which contains a precursor group for pyridine ring formation reaction ($F_2$), through metal coupling. If the aromatic system C contains $F_3$, it will then be transformed to $F_4$ by functional group transformation reaction. The resultant products is then reacted with aromatic system A, which contains a methoxy group and a precursor group for pyridine ring formation ($F_6$) by pyridine ring formation reaction. (If aromatic system A with $F_6$ is not commercially available, a functional group transformation reaction will be performed to transform the precursor group for making $F_5(F_6)$ to $F_6$.) Finally, the methoxy group is transformed to hydroxyl group by demethylation reaction.

Example 402

Preparation of Ligand 201

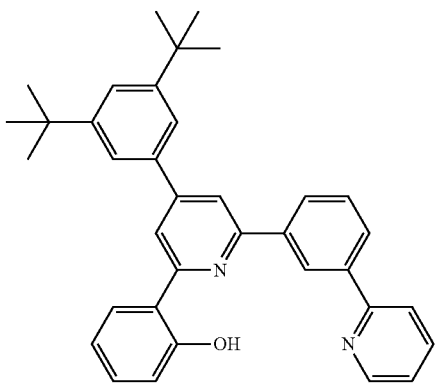 [SMILES: CC(C)(C)c1cc(-c2cc(-c3cccc(-c4ccccn4)c3)nc(-c3ccccc3O)c2)cc(C(C)(C)C)c1]

Ligand 201 was prepared by the procedures in Example 401 with:

A: benzene; C: benzene; D: pyridine; $F_1$: boronic acid; $F_2$: triflate; $F_3$: acetyl; $F_4$: 1-(2-oxoethyl)-pyridinium iodide; $F_5$: acetyl; $F_6$: 3-[3,5-bis(tert-butyl)phenyl]-2-Propenal; coupling reaction: Suzuki reaction; functional group transformation 1: pyridinium salt formation reaction; functional group transformation 2: alpha beta unsaturated ketone formation reaction; pyridine ring formation: reaction in the presence of ammonium acetate and methanol; demethylation: melting pyridine hydrogen chloride. Yield: 72%. $^1$H NMR (500 MHz, CDCl$_3$): 1.43 (s, 18H), 6.98 (t, J=8.1 Hz, 1H), 7.08 (d, J=8.6 Hz, 1H), 7.26-7.28 (m, 1H), 7.36 (t, J=8.4 Hz, 1H), 7.53 (s, 2H), 7.60 (s, 1H), 7.67 (t, J=7.8 Hz, 1H), 7.82 (t, J=7.2 Hz, 1H), 7.85 (d, J=7.4 Hz, 1H), 7.90 (s, 1H), 7.95 (d, J=8.1 Hz, 1H), 8.04 (s, 1H), 8.07 (d, J=8.4 Hz, 1H), 8.13 (d, J=7.8 Hz, 1H), 8.59 (s, 1H), 8.73 (d, J=7.4 Hz, 1H), 14.84 (s, 1H). MS (EI, +ve): 513 (M$^+$).

Example 403

Preparation of Ligand 202

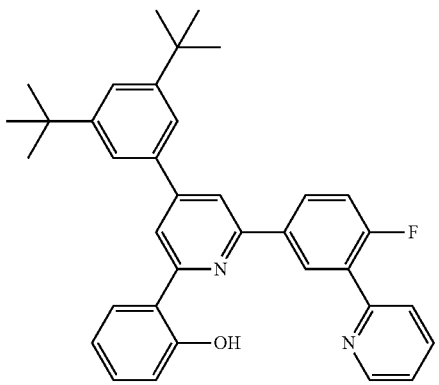 [SMILES: CC(C)(C)c1cc(-c2cc(-c3ccc(F)c(-c4ccccn4)c3)nc(-c3ccccc3O)c2)cc(C(C)(C)C)c1]

Ligand 202 was prepared by the procedures in Example 401 with:

A: benzene; C: fluorobenzene; D: pyridine; $F_1$: boronic acid; $F_2$: triflate; $F_3$: acetyl; $F_4$: 1-(2-oxoethyl)-pyridinium iodide; $F_5$: acetyl; $F_6$: 3-[3,5-bis(tert-butyl)phenyl]-2-Propenal; coupling reaction: Suzuki reaction; functional group transformation 1: pyridinium salt formation reaction; functional group transformation 2: alpha beta unsaturated ketone formation reaction; pyridine ring formation: reaction in the presence of ammonium acetate and methanol; demethylation: melting pyridine hydrogen chloride. Yield: 60%. $^1$H NMR (500 MHz, CDCl$_3$, 25° C.): δ=1.42 (s, 18H, $^t$Bu), 6.97 (t, J=8.1 Hz, 1H), 7.07 (d, J=7.1 Hz, 1H), 7.28-7.31 (m, 1H), 7.33-7.37 (m, 2H), 7.51 (s, 2H), 7.59 (s, 1H), 7.78-7.82 (m, 1H), 7.85-7.87 (m, 2H), 7.93 (d, J=6.6 Hz, 1H), 8.02 (s, 1H), 8.04-8.08 (m, 1H), 8.55-8.58 (m, 1H), 8.75-8.77 (m, 1H), 15.02 (s, 1H, —OH).

Example 404

Preparation of Ligand 203

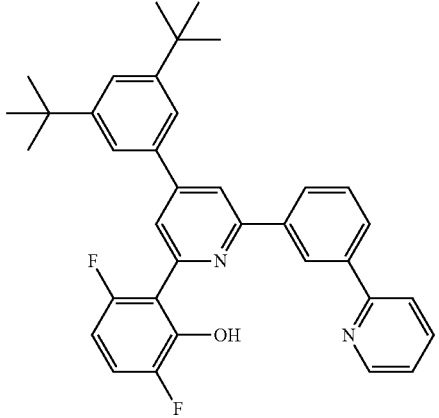 [SMILES: CC(C)(C)c1cc(-c2cc(-c3cccc(-c4ccccn4)c3)nc(-c3c(F)ccc(F)c3O)c2)cc(C(C)(C)C)c1]

Ligand 203 was prepared by the procedures in Example 401 with:

A: paradifluorobenzene; C: benzene; D: pyridine; $F_1$: boronic acid; $F_2$: triflate; $F_3$: acetyl; $F_4$: 1-(2-oxoethyl)-pyridinium iodide; $F_5$: acetyl; $F_6$: 3-[3,5-bis(tert-butyl)phenyl]-2-Propenal; coupling reaction: Suzuki reaction; functional group transformation 1: pyridinium salt formation reaction; functional group transformation 2: alpha beta unsaturated ketone formation reaction; pyridine ring formation: reaction in the presence of ammonium acetate and methanol; demethylation: melting pyridine hydrogen chloride. Yield: 77%. $^1$H NMR (400 MHz, CDCl$_3$, 25° C.): δ=1.43 (s, 18H, $^t$Bu), 6.96-7.01 (m, 1H), 7.28-7.31 (m, 1H), 7.43-7.46 (m, 1H), 7.51 (s, 2H), 7.61 (s, 1H), 7.67 (t, J=7.8 Hz, 1H), 7.82-7.86 (m, 2H), 7.93 (s, 1H), 7.96 (s, 1H), 8.06 (d, J=7.1 Hz, 1H), 8.14 (d, J=7.8 Hz, 1H), 8.57 (s, 1H), 8.73 (d, J=3.8 Hz, 1H), 15.02 (s, 1H, —OH). $^{19}$F NMR (376 MHz, CDCl$_3$, 25° C.): δ=−123.5, −132.5.

Example 405

Preparation of Ligand 204

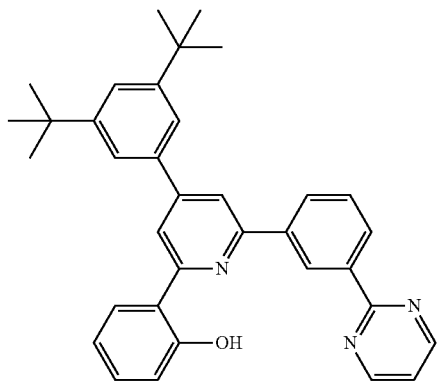 [SMILES: CC(C)(C)c1cc(-c2cc(-c3cccc(-c4ncccn4)c3)nc(-c3ccccc3O)c2)cc(C(C)(C)C)c1]

Ligand 204 was prepared by the procedures in Example 401 with:

A: benzene; C: benzene; D: pyrimidine; $F_1$: boronic acid; $F_2$: bromide; $F_3$: acetyl; $F_4$: 1-(2-oxoethyl)-pyridinium iodide; $F_5$: acetyl; $F_6$: 3-[3,5-bis(tert-butyl)phenyl]-2-Propenal; coupling reaction: Suzuki reaction; functional group transformation 1: pyridinium salt formation reaction; functional group transformation 2: alpha beta unsaturated ketone formation reaction; pyridine ring formation: reaction in the presence of ammonium acetate and methanol; demethylation: melting pyridine hydrogen chloride. Yield: 72%. $^1$H NMR (400 MHz, CDCl$_3$, 25° C.): δ=1.43 (s, 18H, $^t$Bu), 6.97 (t, J=7.1 Hz, 1H), 7.09 (d, J=8.2 Hz, 1H), 7.22-7.25 (m, 1H), 7.36 (t, J=8.3 Hz, 1H), 7.53 (s, 2H), 7.60 (s, 1H), 7.69 (t, J=7.8 Hz, 1H), 7.93-7.96 (m, 2H), 8.04 (s, 1H), 8.16 (d, J=7.7 Hz, 1H), 8.58 (d, J=7.9 Hz, 1H), 8.86 (d, J=7.9 Hz, 2H), 9.06 (s, 1H), 14.82 (s, 1H, —OH).

Example 406

Preparation of Ligand 205

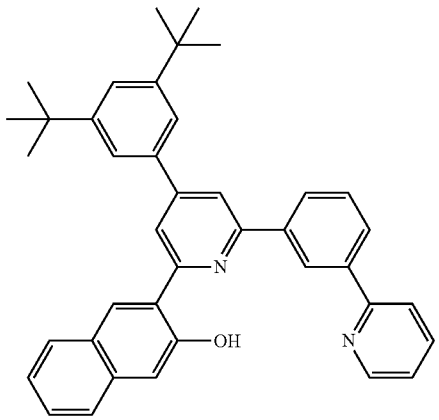 [SMILES: CC(C)(C)c1cc(-c2cc(-c3cccc(-c4ccccn4)c3)nc(-c3cc4ccccc4cc3O)c2)cc(C(C)(C)C)c1]

Ligand 205 was prepared by the procedures in Example 401 with:

A: naphthalene; C: benzene; D: pyridine; $F_1$: boronic acid; $F_2$: triflate; $F_3$: acetyl; $F_4$: 1-(2-oxoethyl)-pyridinium iodide; $F_5$: acetyl; $F_6$: 3-[3,5-bis(tert-butyl)phenyl]-2-Propenal; coupling reaction: Suzuki reaction; functional group transformation 1: pyridinium salt formation reaction; functional group transformation 2: alpha beta unsaturated ketone formation reaction; pyridine ring formation: reaction in the presence of ammonium acetate and methanol; demethylation: melting pyridine hydrogen chloride. Yield: 77%. $^1$H NMR (400 MHz, CDCl$_3$, 25° C.): δ=1.45 (s, 18H, $^t$Bu), 7.27-7.32 (m, 2H), 7.42 (s, 1H), 7.47 (t, J=6.9 Hz, 1H), 7.56 (s, 2H), 7.63 (s, 1H), 7.70 (t, J=7.7 Hz, 1H), 7.74 (d, J=8.3 Hz, 1H), 7.82-7.88 (m, 3H), 7.96 (s, 1H), 8.12 (d, J=6.9 Hz, 1H), 8.17 (d, J=7.8 Hz, 1H), 8.23 (s, 1H), 8.47 (s, 1H), 8.62 (s, 1H), 8.76 (d, J=4.0 Hz, 1H), 14.52 (s, 1H, —OH).

Example 407

Preparation of Ligand 206

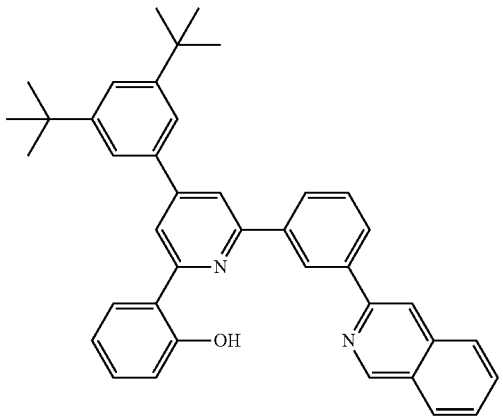 [SMILES: CC(C)(C)c1cc(-c2cc(-c3cccc(-c4cc5ccccc5cn4)c3)nc(-c3ccccc3O)c2)cc(C(C)(C)C)c1]

Ligand 207 was prepared by the procedures in Example 401 with:

A: benzene; C: benzene; D: isoquinoline; $F_1$: boronic acid; $F_2$: triflate; $F_3$: acetyl; $F_4$: 1-(2-oxoethyl)-pyridinium iodide; $F_5$: acetyl; $F_6$: 3-[3,5-bis(tert-butyl)phenyl]-2-Propenal; coupling reaction: Suzuki reaction; functional group transformation 1: pyridinium salt formation reaction; functional group transformation 2: alpha beta unsaturated ketone formation reaction; pyridine ring formation: reaction in the presence of ammonium acetate and methanol; demethylation: melting pyridine hydrogen chloride. Yield: 77%. $^1$H NMR (500 MHz, CDCl$_3$): 1.44 (s, 18H), 6.98 (t, J=8.1 Hz, 1H), 7.09 (d, J=8.6 Hz, 1H), 7.35 (t, J=8.4 Hz, 1H), 7.55 (s, 2H), 7.60-7.73 (m, 4H), 7.92-8.09 (m, 6H), 8.19 (s, 1H), 8.27 (d, J=7.8 Hz, 1H), 8.72 (s, 1H), 9.38 (s, 1H), 14.88 (s, 1H). MS (EI, +ve): 563 (M$^+$).

Example 408

Preparation of Ligand 207

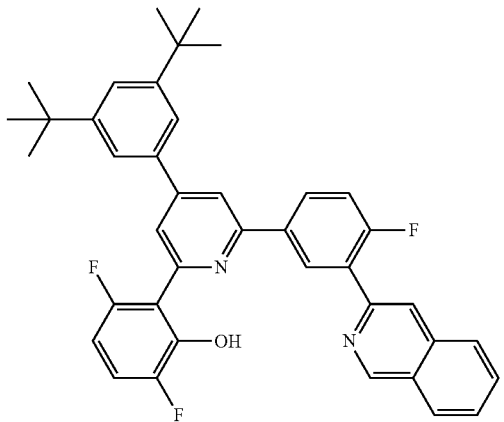 [SMILES: CC(C)(C)c1cc(-c2cc(-c3ccc(F)c(-c4cc5ccccc5cn4)c3)nc(-c3c(F)ccc(F)c3O)c2)cc(C(C)(C)C)c1]

Ligand 208 was prepared by the procedures in Example 401 with:

A: paradifluorobenzene; C: fluorobenzene; D: isoquinoline; F$_1$: boronic acid; F$_2$: triflate; F$_3$: acetyl; F$_4$: 1-(2-oxoethyl)-pyridinium iodide; F$_5$: acetyl; F$_6$: 3-[3,5-bis(tert-butyl)phenyl]-2-Propenal; coupling reaction: Suzuki reaction; functional group transformation 1: pyridinium salt formation reaction; functional group transformation 2: alpha beta unsaturated ketone formation reaction; pyridine ring formation: reaction in the presence of ammonium acetate and methanol; demethylation: melting pyridine hydrogen chloride. Yield: 60%. $^1$H NMR (500 MHz, CDCl$_3$): 1.43 (s, 18H), 6.95-7.01 (m, 1H), 7.09 (d, J=8.6 Hz, 1H), 7.36-7.45 (m, 2H), 7.51 (s, 2H), 7.61 (s, 1H), 7.65 (t, J=7.4 Hz, 1H), 7.75 (t, J=7.4 Hz, 1H), 7.91-8.06 (m, 5H), 8.28 (s, 1H), 8.75 (m, 1H), 9.38 (s, 1H), 15.02 (s, 1H). $^{19}$F NMR (376 MHz, CDCl$_3$): −114.93, −123.42, −132.54. MS (EI, +ve): 617 (M$^+$).

Example 409

Preparation of Ligand 208

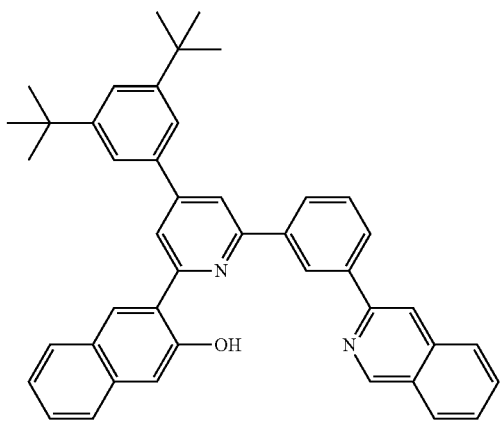 [SMILES: CC(C)(C)c1cc(-c2cc(-c3cccc(-c4cc5ccccc5cn4)c3)nc(-c3cc4ccccc4cc3O)c2)cc(C(C)(C)C)c1]

A: naphthalene; C: benzene; D: isoquinoline; F$_1$: boronic acid; F$_2$: triflate; F$_3$: acetyl; F$_4$: 1-(2-oxoethyl)-pyridinium iodide; F$_5$: acetyl; F$_6$: 3-[3,5-bis(tert-butyl)phenyl]-2-Propenal; coupling reaction: Suzuki reaction; functional group transformation 1: pyridinium salt formation reaction; functional group transformation 2: alpha beta unsaturated ketone formation reaction; pyridine ring formation: reaction in the presence of ammonium acetate and methanol; demethylation: melting pyridine hydrogen chloride. Yield: 72%. $^1$H NMR (400 MHz, CDCl$_3$, 25° C.): δ=1.46 (s, 18H, $^t$Bu), 7.32 (t, J=7.1 Hz, 1H), 7.43 (s, 1H), 7.44 (t, J=7.1 Hz, 1H), 7.58 (s, 2H), 7.62-7.64 (m, 2H), 7.70-7.75 (m, 3H), 7.87 (d, J=8.1 Hz, 1H), 7.94 (d, J=8.1 Hz, 1H), 8.00 (s, 1H), 8.03 (d, J=8.3 Hz, 1H), 8.12 (d, J=7.9 Hz, 1H), 8.21 (s, 1H), 8.24 (s, 1H), 8.29 (d, J=7.9 Hz, 1H), 8.48 (s, 1H), 8.75 (s, 1H), 9.39 (s, 1H), 14.49 (s, 1H, —OH).

Example 410

Preparation of Ligand 209

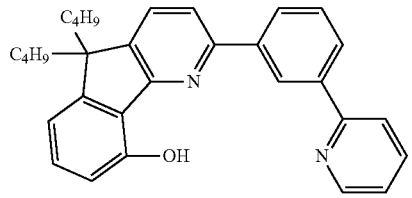

Ligand 210 was prepared by the procedures in Example 401 with:

A: 1-Indanone; C: benzene; D: pyridine; F$_1$: boronic acid; F$_2$: triflate; F$_3$: nil; F$_4$: acetyl; F$_5$: proton; F$_6$: N,N-dimethylethenamine; coupling reaction: Suzuki reaction; functional group transformation 1: nil; functional group transformation 2: reaction with dimethylacetamide; pyridine ring formation: a) reaction in the presence of potassium tert-butoxide and THF b) remove THF and reaction in the presence of ammonium acetate and methanol c) addition of butyl chains by reaction with 1-bromobutane in the presence of potassium tert-butoxide; demethylation: melting pyridine hydrogen chloride. Yield: 65%. $^1$H NMR (500 MHz, CDCl$_3$): 0.70-0.73 (m, 10H), 1.09-1.16 (m, 4H), 1.97-2.03 (m, 4H), 6.90-6.94 (m, 2H), 7.28-7.29 (m, 1H), 7.33 (t, J=7.8 Hz, 1H), 7.62 (t, J=7.7 Hz, 1H), 7.70-7.71 (m, 2H), 7.80 (t, J=8.5 Hz), 7.85 (d, J=7.9 Hz, 1H), 8.06-8.11 (m, 2H), 8.65 (s, 1H), 8.75 (d, J=4.7 Hz, 1H), 9.52 (s, br, 1H). MS (EI, +ve): 449 [M$^+$].

Example 411

Preparation of Ligand 210

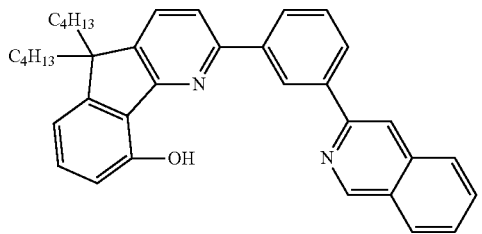

Ligand 211 was prepared by the procedures in Example 401 with:

A: 1-Indanone; C: benzene; D: isoquinoline; $F_1$: boronic acid; $F_2$: triflate; $F_3$: nil; $F_4$: acetyl; $F_5$: proton; $F_6$: N,N-dimethylethenamine; coupling reaction: Suzuki reaction; functional group transformation 1: nil; functional group transformation 2: reaction with dimethylacetamide; pyridine ring formation: a) reaction in the presence of potassium tert-butoxide and THF b) remove THF and reaction in the presence of ammonium acetate and methanol c) addition of hexyl chains by reaction with 1-bromohexane in the presence of potassium tert-butoxide; demethylation: melting pyridine hydrogen chloride. Yield: 73%. $^1$H NMR (500 MHz, $CDCl_3$): 0.72-0.80 (m, 10H), 1.05-1.17 (m, 12H), 1.95-2.05 (m, 4H), 6.92-6.95 (m, 2H), 7.34 (t, J=7.8 Hz, 1H), 7.60 (t, J=7.0 Hz, 1H), 7.66 (t, J=7.7 Hz, 1H), 7.71-7.77 (m, 3H), 7.91 (d, J=8.1 Hz, 1H), 8.01 (d, J=7.9 Hz, 1H), 8.11 (d, J=8.0 Hz, 1H), 8.18 (s, 1H), 8.21 (d, J=7.9 Hz, 1H), 8.79 (s, 1H), 9.38 (s, 1H), 9.54 (s, br, 1H). $^{13}$C NMR (126 MHz, $CD_2Cl_2$): 13.98, 22.54, 24.02, 29.66, 31.48, 39.70, 54.32, 113.17, 114.25, 116.70, 117.98, 124.36, 125.57, 127.02, 127.18, 127.52, 127.57, 127.89, 129.28, 130.57, 130.91, 130.99, 136.66, 139.57, 140.14, 142.09, 151.04, 152.47, 152.53, 154.44, 155.14, 161.25. MS (EI, +ve): 555 [M$^+$].

Example 412

Preparation of Ligand 211

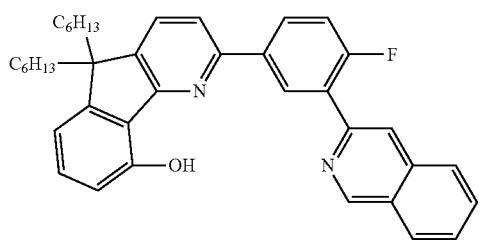

Ligand 212 was prepared by the procedures in Example 401 with:

A: 1-Indanone; C: fluorobenzene; D: isoquinoline; $F_1$: boronic acid; $F_2$: triflate; $F_3$: nil; $F_4$: acetyl; $F_5$: proton; $F_6$: N,N-dimethylethenamine; coupling reaction: Suzuki reaction; functional group transformation 1: nil; functional group transformation 2: reaction with dimethylacetamide; pyridine ring formation: a) reaction in the presence of potassium tert-butoxide and THF b) remove THF and reaction in the presence of ammonium acetate and methanol c) addition of hexyl chains by reaction with 1-bromohexane in the presence of potassium tert-butoxide; demethylation: melting pyridine hydrogen chloride. Yield: 44%. $^1$H NMR (500 MHz, $CDCl_3$): 0.71-0.80 (m, 10H), 1.08-1.18 (m, 12H), 1.92-2.01 (m, 4H), 6.89-6.93 (m, 2H), 7.30-7.37 (m, 2H), 7.65 (t, J=7.5 Hz, 1H), 7.70 (m, 2H), 7.75 (t, J=7.5 Hz, 1H), 7.92 (d, J=8.2 Hz, 1H), 8.03 (d, J=8.1 Hz, 1H), 8.09-8.12 (m, 1H).

Example 413

Preparation of Ligand 219

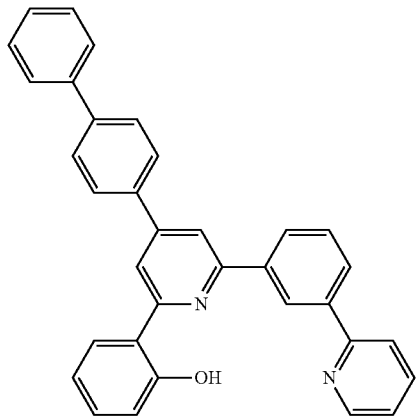 [SMILES: Oc1ccccc1-c1cc(-c2ccc(-c3ccccc3)cc2)cc(-c2cccc(-c3ccccn3)c2)n1]

Ligand 220 was prepared by the procedures in Example 401 with:

A: benzene; C: benzene; D: pyridine; $F_1$: boronic acid; $F_2$: triflate; $F_3$: acetyl; $F_4$: 1-(2-oxoethyl)-pyridinium iodide; $F_5$: acetyl; $F_6$: 4,4'-biphenyl-2-Propenal; coupling reaction: Suzuki reaction; functional group transformation 1: pyridinium salt formation reaction; functional group transformation 2: alpha beta unsaturated ketone formation reaction; pyridine ring formation: reaction in the presence of ammonium acetate and methanol; demethylation: melting pyridine hydrogen chloride. Yield: 72%. $^1$H NMR (500 MHz, $CD_2Cl_2$, 25° C.): δ=6.99 (t, J=8.2 Hz, 1H), 7.05 (d, J=8.3 Hz, 1H), 7.29-7.32 (m, 1H), 7.32-7.38 (m, 1H), 7.40-7.43 (m, 1H), 7.49-7.52 (m, 2H), 7.67-7.72 (m, 3H), 7.81-7.86 (m, 3H), 7.89-7.93 (m, 3H), 8.03 (d, J=8.1 Hz, 1H), 8.04 (s, 1H), 8.08-8.10 (m, 1H), 8.16-8.18 (m, 1H), 8.19 (s, 1H), 8.69 (s, 1H), 8.72-8.74 (m, 1H).

Example 414

General Preparation Method for Complexes with Structure I

Refer the FIG. 2, ligand with Structure II is reacted with potassium tetrachloroplatinate in the mixture of acetic acid and chloroform at 118° C. for 24 hours. The product is purified by column chromatography.

Example 415

Preparation of Complex 101

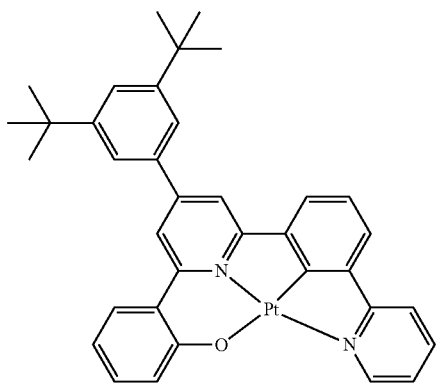

Complex 101 was prepared by Example 410 using Ligand 201. Yield: 80%. $^1$H NMR (500 MHz, CD$_2$Cl$_2$): 1.47 (s, 18H), 6.74 (t, J=6.8 Hz, 1H), 7.24-7.29 (m, 2H), 7.32-7.40 (m, 2H), 7.57 (d, J=7.5 Hz, 1H), 7.66-7.69 (m, 4H), 7.78 (d, J=8.9 Hz, 1H), 7.83 (s, 1H), 7.97 (t, J=7.9 Hz, 1H), 8.17 (d, J=8.5 Hz, 1H), 8.37 (s, 1H), 8.99 (d, J=6.8 Hz, 1H). MS (FAB, +ve): 706 (M$^+$).

Example 416

Preparation of Complex 102

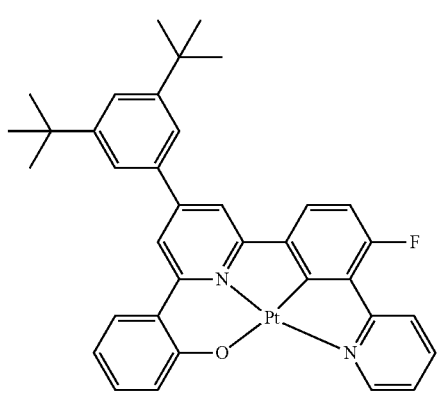

Complex 102 was prepared by Example 410 using Ligand 202. Yield: 70%. $^1$H NMR (400 MHz, CDCl$_3$, 25° C.): δ=1.49 (s, 18H, $^t$Bu), 6.76-6.80 (m, 1H), 6.88-6.93 (m, 1H), 7.36-7.43 (m, 3H), 7.60 (s, 2H), 7.61-7.65 (m, 3H), 7.69 (s, 1H), 7.98-8.01 (m, 2H), 8.14 (d, J=7.3 Hz, 1H), 8.33 (s, 1H), 9.08 (d, J=6.8 Hz, 1H). $^{19}$F NMR (376 MHz, CDCl$_3$, 25° C.): δ=−113.2.

Example 417

Preparation of Complex 103

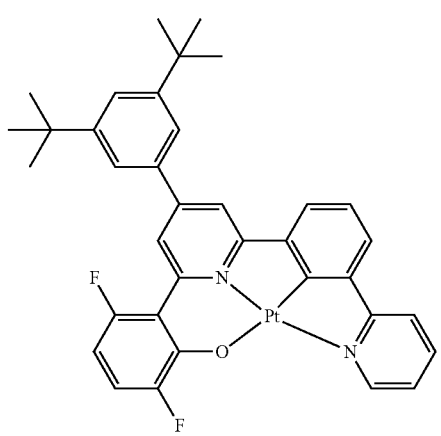

Complex 103 was prepared by Example 410 using Ligand 203. Yield: 80%. $^1$H NMR (500 MHz, DMF, 25° C.): δ 1.43 (s, 18H, $^t$Bu), 7.36-7.41 (m, 1H), 7.52 (t, J=6.0 Hz, 1H), 7.69 (s, 1H), 7.81 (d, J=8.2 Hz, 1H), 7.91 (s, 1H), 8.11-8.15 (m, 2H), 8.22 (t, J=7.8 Hz, 1H), 8.29 (d, J=8.1 Hz, 1H), 8.40 (s, 1H), 8.43 (s, 1H), 8.54 (s, 1H), 9.00 (d, J=5.7 Hz, 1H). $^{19}$F NMR (376 MHz, DMF, 25° C.): δ=−126.6, −129.3.

Example 418

Preparation of Complex 104

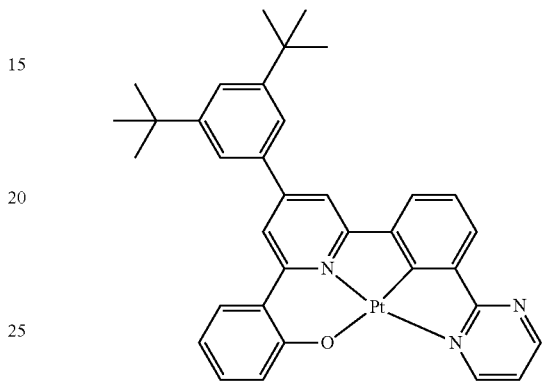

Complex 104 was prepared by Example 410 using Ligand 204. Yield: 80%. $^1$H NMR (400 MHz, CD$_2$Cl$_2$, 25° C.): δ 1.50 (s, 18H, $^t$Bu), 6.74 (t, J=6.9 Hz, 1H), 7.15 (s, 1H), 7.21-7.26 (m, 2H), 7.36 (t, J=6.5 Hz, 1H), 7.67-7.71 (m, 6H), 8.12 (d, J=7.8 Hz, 1H), 8.30 (s, 1H), 8.86 (s, 1H), 9.04 (m, 1H).

Example 419

Preparation of Complex 105

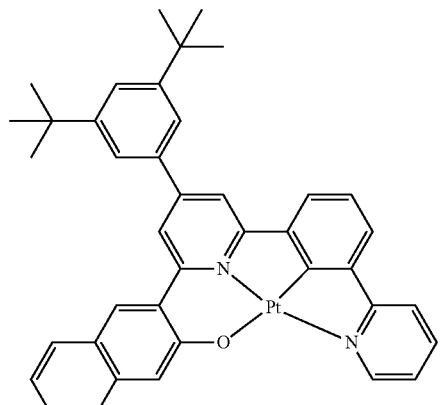

Complex 106 was prepared by Example 410 using Ligand 206. Yield: 60%. $^1$H NMR (400 MHz, CD$_2$Cl$_2$, 25° C.): δ=1.48 (s, 18H, $^t$Bu), 7.13 (t, J=7.0 Hz, 1H), 7.30 (t, J=7.4 Hz, 1H), 7.37-7.43 (m, 2H), 7.58-7.64 (m, 3H), 7.6-7.71 (m, 4H), 7.80-7.84 (m, 2H), 7.93 (s, 1H), 8.03 (t, J=7.7 Hz, 1H), 8.54 (s, 1H), 8.69 (s, 1H), 9.0-9.04 (m, 1H).

Example 420

Preparation of Complex 106

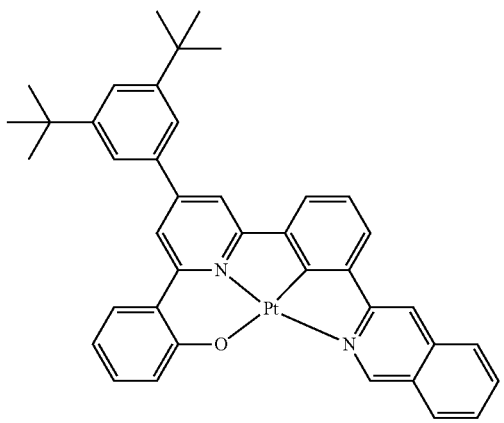

Complex 107 was prepared by Example 410 using Ligand 207. Yield: 80%. $^1$H NMR (500 MHz, CD$_2$Cl$_2$): 1.48 (s, 18H), 6.74 (t, J=6.8 Hz, 1H), 7.28-7.42 (m, 3H), 7.60-7.70 (m, 6H), 7.80-7.90 (m, 3H), 8.03 (s, 1H), 8.13-8.17 (m, 2H), 8.35 (s, 1H), 9.65 (s, 1H). MS (FAB, +ve): 756 (M$^+$).

Example 421

Preparation of Complex 107

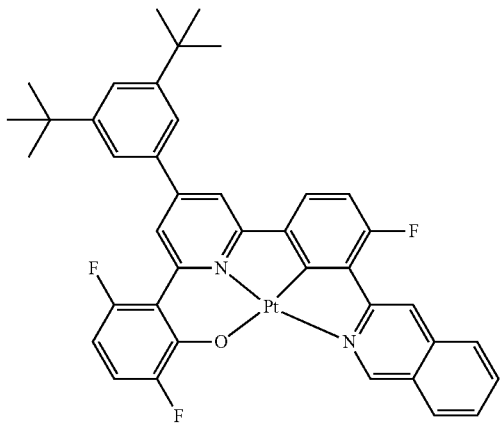

Complex 108 was prepared by Example 410 using Ligand 208. Yield: 65%. $^1$H NMR (400 MHz, CDCl$_3$, 25° C.): δ=1.49 (s, 18H, $^t$Bu), 6.68-6.73 (m, 1H), 6.82-6.87 (m, 1H), 7.28-7.29 (m, 1H), 7.34-7.36 (m, 1H), 7.39 (s, 1H), 7.56 (s, 2H), 7.62-7.66 (m, 2H), 7.75-7.82 (m, 2H), 7.95-8.01 (m, 3H), 9.32 (s, 1H). $^{19}$F NMR (376 MHz, CDCl$_3$, 25° C.): δ=−113.8, −126.3, −129.7.

Example 422

Preparation of Complex 108

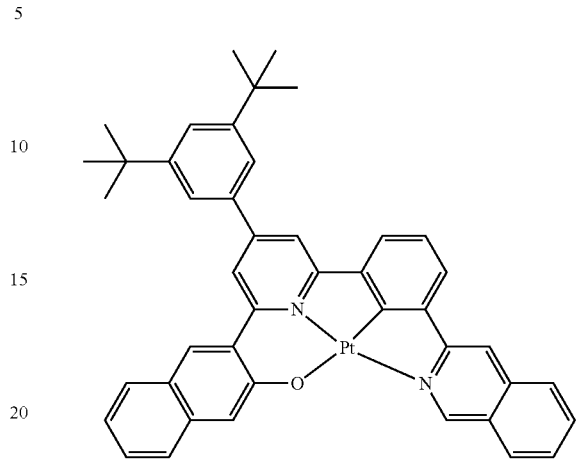

Complex 109 was prepared by Example 410 using Ligand 209. Yield: 60%. $^1$H NMR (400 MHz, CDCl$_3$, 25° C.): δ=1.54 (s, 18H, $^t$Bu), 6.88-6.93 (m, 2H), 7.01 (t, J=7.5 Hz, 1H), 7.06-7.11 (m, 2H), 7.16-7.21 (m, 3H), 7.30 (t, J=6.7 Hz, 1H), 7.50 (d, J=8.2 Hz, 1H), 7.59-7.63 (m, 4H), 7.72 (s, 1H), 8.01 (d, J=8.1 Hz, 1H), 8.58 (s, 1H), 8.68 (s, 1H), 8.80 (s, 1H).

Example 423

Preparation of Complex 109

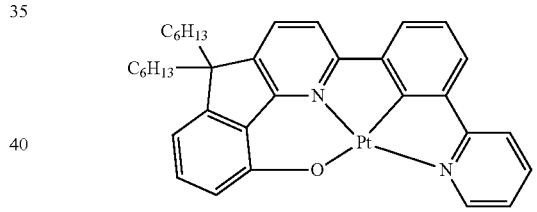

Complex 110 was prepared by Example 410 using Ligand 210. Yield: 65%. $^1$H NMR (500 MHz, CD$_2$Cl$_2$): 0.69-0.80 (m, 10H), 1.10-1.18 (m, 4H), 2.00-2.15 (m, 4H), 6.75 (d, J=7.1 Hz, 1H), 7.19 (d, J=8.4 Hz, 1H), 7.26 (t, J=7.6 Hz, 1H), 7.36 (t, J=6.0 Hz, 1H), 7.49-7.53 (m, 2H), 7.57 (d, J=7.6 Hz, 1H), 7.63 (d, J=7.6 Hz, 1H), 7.75 (d, J=7.9 Hz, 1H), 7.92 (t, J=7.7 Hz, 1H), 7.96 (d, J=7.7 Hz, 1H), 9.12 (d, J=5.3 Hz, 1H). MS (FAB, +ve): 642 [M$^+$].

Example 424

Preparation of Complex 110

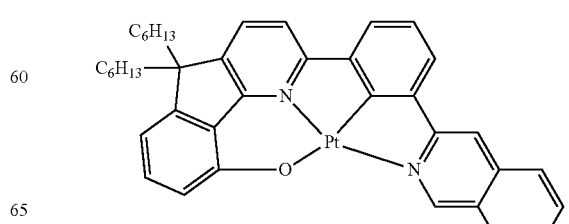

Complex 111 was prepared by Example 410 using Ligand 211. Yield: 70%. $^1$H NMR (500 MHz, CD$_2$Cl$_2$): 0.76-0.85 (m, 10H), 1.03-1.19 (m, 12H), 2.01-2.13 (m, 4H), 6.74 (d, J=7.0 Hz, 1H), 7.16 (d, J=7.2 Hz, 1H), 7.28 (t, J=7.5 Hz, 1H), 7.52-7.63 (m, 5H), 7.77-7.80 (m, 1H), 7.89 (d, J=7.8 Hz, 1H), 7.96 (d, J=7.6 Hz, 1H), 8.08 (s, 1H), 8.14 (d, J=7.9 Hz, 1H), 9.74 (s, 1H). $^{13}$C NMR (126 MHz, CD$_2$Cl$_2$): 13.72, 22.52, 24.05, 29.67, 31.49, 39.91, 55.38, 108.18, 113.77, 116.10, 119.30, 122.32, 122.54, 122.62, 125.70, 126.85, 127.68, 127.98, 128.60, 129.09, 132.51, 132.84, 136.64, 140.91, 141.41, 143.53, 153.74, 153.88, 154.50, 157.73, 160.81, 160.89, 162.73. MS (FAB, +ve): 748 [M$^+$].

Example 425

Preparation of Complex 111

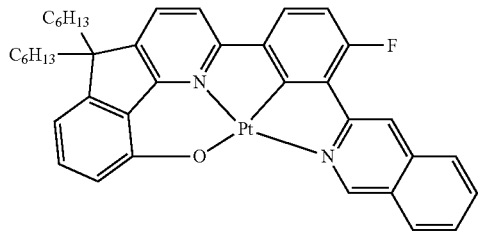

Complex 112 was prepared by Example 410 using Ligand 212. Yield: 80%. $^1$H NMR (500 MHz, CDCl$_3$): 0.68-0.77 (m, 10H), 1.02-1.12 (m, 12H), 2.00-2.07 (m, 4H), 6.71 (d, J=7.0 Hz, 1H), 7.00 (dd, J=8.4 Hz, $^3$J$_{F-H}$=11.9 Hz, 1H), 7.27 (d, J=7.6 Hz, 1H), 7.47 (d, J=7.6 Hz, 1H), 7.54 (t, J=7.8 Hz, 1H), 7.62 (dd, J=8.3 Hz, $^4$J$_{F-H}$=3.9 Hz, 1H), 7.71 (t, J=8.6 Hz, 1H), 7.87 (t, J=8.6 Hz, 1H), 7.90 (d, J=7.7 Hz, 1H), 7.97 (d, J=8.1 Hz, 1H), 8.18 (d, J=8.1 Hz, 1H), 8.43 (s, 1H), 9.84 (s, 1H). $^{19}$F NMR (376 MHz, CDCl$_3$): −114.17. MS (FAB, +ve): 766 [M$^+$].

Example 426

Preparation of Complex 119

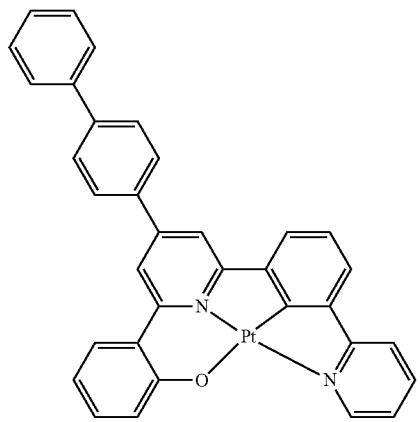

Complex 120 was prepared by Example 410 using Ligand 220. Yield: 60%. $^1$H NMR (400 MHz, CD$_2$Cl$_2$, 25° C.): δ=6.75 (t, J=8.1 Hz, 1H), 7.25 (t, J=7.6 Hz, 1H), 7.30 (d, J=8.4 Hz, 1H), 7.36-7.46 (m, 3H), 7.51-7.58 (m, 2H), 7.65 (d, J=7.6 Hz, 1H), 7.73-7.79 (m, 3H), 7.84 (d, J=8.3 Hz, 2H), 7.88 (s, 1H), 7.96-8.00 (m, 3H), 8.18 (d, J=7.4 Hz, 1H), 8.42 (s, 1H), 8.95 (d, J=4.8 Hz, 1H).

Example 427

Photophysical Properties for Complex 101-Complex 112

| | Absorption λ$_{max}$ (molar extinction coefficient) | Emission λ$_{max}$ (dichloromethane solution) | Solution quantum Yield |
|---|---|---|---|
| Complex 101 | 242 (37400); 285 (38400); 372 (13800); 437 (sh) 5600 | 502 | 0.76 |
| Complex 102 | 242 (4.19), 253 (4.07), 284 (4.45), 301 (3.52), 363 (1.71), 400 (1.14), 424 (0.86) | 511 | 0.83 |
| Complex 103 | 242 (3.65), 287 (3.88), 370 (1.59), 425 (0.73) | 526 | 0.71 |
| Complex 106 | 248 (5.72), 285 (5.30), 300 (5.23), 381 (1.79), 419 (0.92), 494 (0.26) | 528 | 0.17 |
| Complex 107 | 248 (4.20), 259 (4.24), 284 (3.84), 296 (3.92), 380 (1.65), 441 (0.32) | 534 | 0.61 |
| Complex 108 | 292 (56100); 303 (49500); 369 (25600); 403 (10600); 445 (sh) (2400) | 523 | 0.60 |
| Complex 109 | 252 (6.45), 288 (5.36), 374 (1.52), 398 (1.49), 530 (0.18) | 661 | 0.019 |
| Complex 110 | 254 (39800); 354 (15400); 390 (12700); 424 (sh) (8186) | 496 | 0.63 |
| Complex 111 | 255 (55300); 275 (47900); 293 (35600); 364 (20800); 398 (16300); 427 (sh) (5900) | 528 | 0.38 |
| Complex 112 | 273 (56900); 290 (41800); 357 (21800); 393 (17400); 415 (sh) (9400) | 517 | 0.47 |

Example 428

General Thermal Deposition OLED Fabrication Method

On an anode coated transparent substrate, hole transporting layer(s), emitting layer(s), electron transporting layer(s), electron injection layer and a metal cathode were deposited sequentially under a high vacuum environment (pressure<1×10$^{-6}$ torr).

Example 429

A device fabricated with example 428 wherein the hole transporting layers are 10 nm of N,N'-Bis(naphthalen-1-yl)-N,N'-bis(phenyl)-benzidine (NPB) and 30 nm of 4,4',4"-tris(carbazol-9-yl)triphenylamine (TCTA), the emitting layer is 30 nm of complex 101 doped TCTA layer (2.8% complex 101), the electron transporting layer is 30 nm of 2,9-Dimethyl-4,7-diphenyl-1,10-phenanthroline (BCP), the electron injection layer is 1 nm of lithium fluoride and the metal cathode is 100 nm of aluminum.

Example 430

A device fabricated with Example 428 wherein the hole transporting layer is 40 nm of NPB, the emitting layer is 20 nm of complex 106 doped 4,4'-Bis(carbazol-9-yl)biphenyl (CBP) layer (4.4% complex 106), the electron transporting layers are 15 nm of BCP and 30 nm of Tris(8-hydroxyquinolinato)aluminium (Alq), the electron injection layer is 1 nm of lithium fluoride and the metal cathode is 100 nm of aluminum.

Example 431

A device fabricated with Example 428 wherein the hole transporting layer is 40 nm of NPB, the emitting layer is 20 nm of complex 110 doped 1,3-Bis(carbazol-9-yl)benzene (mCP) layer (4.9% complex 110), the electron transporting layer is 30 nm of BCP, the electron injection layer is 1 nm of lithium fluoride and the metal cathode is 100 nm of aluminum.

Example 432

A device fabricated with Example 428 wherein the hole transporting layer is 40 nm of NPB, the emitting layers are 20 nm of complex 110 doped CBP (2.6% complex 110) and 20 nm complex 110 doped 2,2',2"-(1,3,5-Benzinetriyl)-tris(1-phenyl-1-H-benzimidazole) (TPBi; 2.9% complex 107) layers, the electron transporting layer is 30 nm of BCP, the electron injection layer is 1 nm of lithium fluoride and the metal cathode is 100 nm of aluminum.

Example 433

A device fabricated with Example 428 wherein the hole transporting layer is 40 nm of NPB, the emitting layers are 20 nm of complex 101 doped mCP (3.1% complex 101) and 20 nm complex 101 doped CBP (3.5% complex 101) layers, the electron transporting layer is 30 nm of BCP, the electron injection layer is 1 nm of lithium fluoride and the metal cathode is 100 nm of aluminum.

Example 434

A device fabricated with Example 428 wherein the hole transporting layer is 40 nm of NPB, the emitting layers are 20 nm of complex 101 doped TCTA (1.3% complex 101), 10 nm complex 101 doped CBP (1.2% complex 101) and 20 nm complex 101 doped TPBi (1.5% complex 101) layers, the electron transporting layer is 30 nm of BCP, the electron injection layer is 1 nm of lithium fluoride and the metal cathode is 100 nm of aluminum.

Example 435

A device fabricated with Example 428 wherein the hole transporting layer is 40 nm of NPB, the emitting layers are 20 nm of complex 101 doped TCTA (1.1% complex 101) and 20 nm complex 101 doped TPBi (1.2% complex 101) layers, the electron transporting layer is 30 nm of BCP, the electron injection layer is 1 nm of lithium fluoride and the metal cathode is 100 nm of aluminum.

Example 436

A device fabricated with Example 428 wherein the hole transporting layer is 40 nm of NPB, the emitting layer is 100 nm of complex 101 doped CBP (1.1% complex 101) layer, the electron transporting layer is 30 nm of BCP, the electron injection layer is 1 nm of lithium fluoride and the metal cathode is 100 nm of aluminum.

Example 439

Fabrication of Single Emitter WOLED

A single emitter WOLED fabricated with Example 428 wherein the hole transporting layer is 40 nm of NPB, the emitting layer is 30 nm of complex 224 doped mCP (9% complex 224) layer, the electron transporting layer is 40 nm of BAlQ, the electron injection layer is 0.5 nm of lithium fluoride and the metal cathode is 80 nm of aluminum.

Example 437

The performances for the devices in above examples are shown below:

| Example | EL $\lambda_{max}$ | CIE | Efficiency$_{max}$ cd/A@ current density mA/cm$^2$ |
|---|---|---|---|
| 429 | 512 | 0.31, 0.61 | 7.59/3.53 |
| 430 | 543 | 0.39, 0.58 | 20.7/1.05 |
| 431 | | | 10.5/0.76 |
| 432 | 524 | 0.34, 0.56 | 11.9/0.15 |
| 433 | 516 | 0.31, 0.59 | 10.7/1.91 |
| 434 | 508 | 0.26, 0.63 | 17.3/7.0 |
| 435 | 512 | 0.26, 0.64 | 12.6/1.14 |
| 436 | 512 | 0.26, 0.64 | 22.2/0.58 |
| 439 | 483, 619 | 0.37, 0.43 | 36.4/0.021 |

Example 438

Solution Process OLED Fabrication

A layer of poly(3,4-ethylenedioxythiophene):poly(styrenesulfonic acid) (PEDOT:PPS) (~40 nm) was deposition on indium tin oxide (ITO) glass by spin coating and dried in an oven. 5% complex 101 in PVK was dissolved in chlorobenzene in 20 mg/mL ratio. The 5% complex 101 doped PVK was spin coated on the top of PEDOT:PPS layer and dried in an oven (~80 nm). 10 nm of BCP, 30 nm of Alq, 1 nm LiF and 100 nm of Al layers were sequentially deposited on top of the polymer layer by thermal deposition (pressure<$1\times10^{-6}$ torr). This device has CIE, brightness$_{max}$ and efficiency$_{max}$ of (0.31, 0.61), 17,800 cdm$^{-2}$ and 10.9 cdA$^{-1}$ respectively.

While the invention has been explained in relation to certain embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. An organometallic complex having a chemical structure of structure I:

Structure I

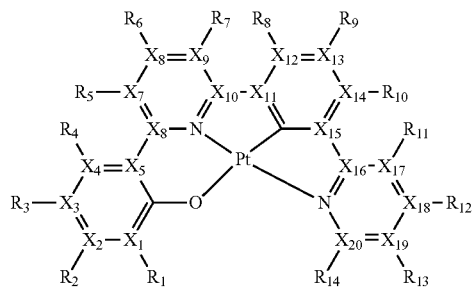

wherein $R_1$-$R_{14}$ are independently hydrogen, halogen, hydroxyl, an unsubstituted alkyl, a substituted alkyl, cycloalkyl, an unsubstituted aryl, a substituted aryl, acyl, alkoxy, acyloxy, amino, nitro, acylamino, aralkyl, cyano, carboxyl, thio, styryl, aminocarbonyl, carbamoyl, aryloxycarbonyl, phenoxycarbonyl, or an alkoxycarbonyl group, each $R_1$-$R_{14}$ can independently form 5-8 member ring(s) with adjacent R group(s), $X_1$-$X_{20}$ are independently boron, carbon, nitrogen, oxygen, or silicon.

2. The organometallic complex of claim 1 is one selected from the group consisting of:

Complex 101

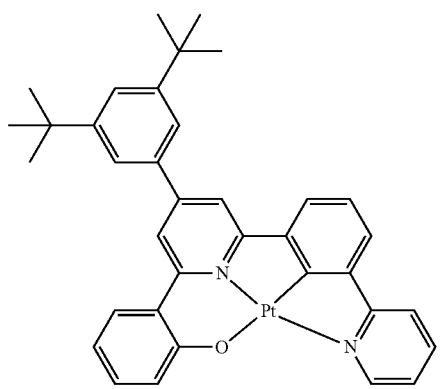

Complex 102

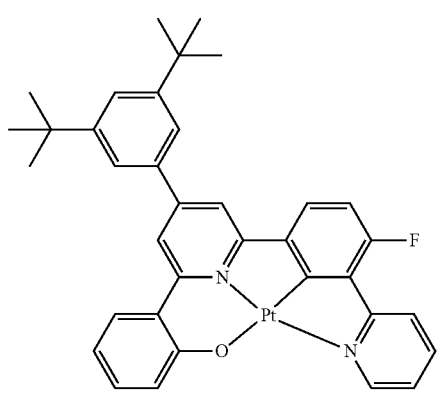

Complex 103

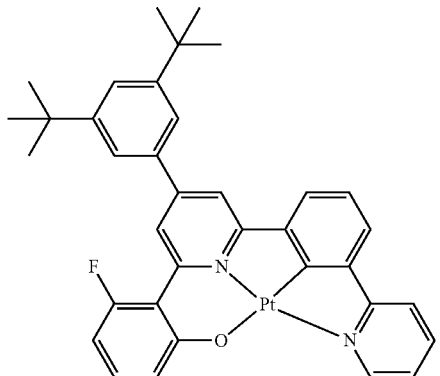

Complex 104

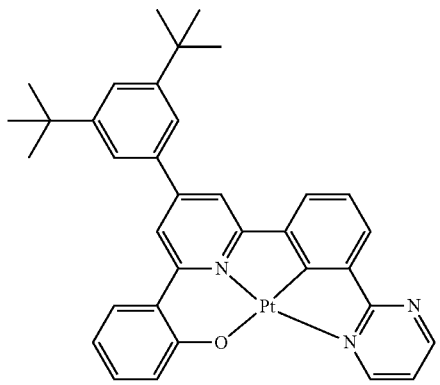

Complex 105

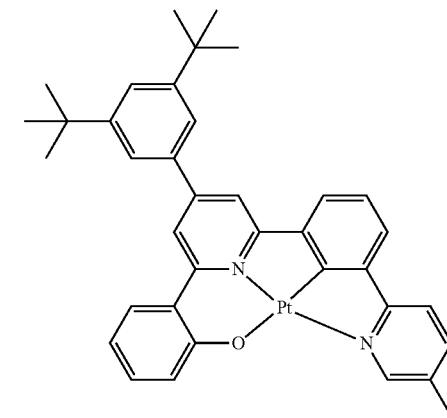

Complex 106

Complex 107
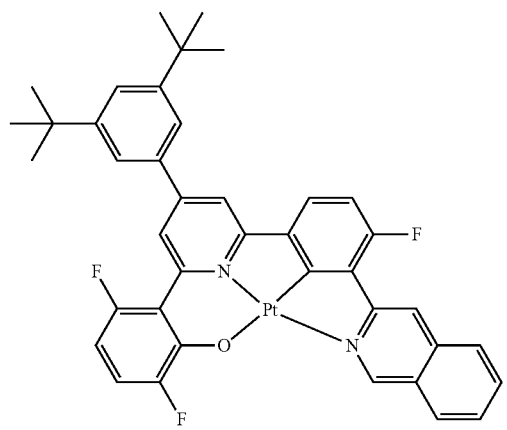
Complex 108
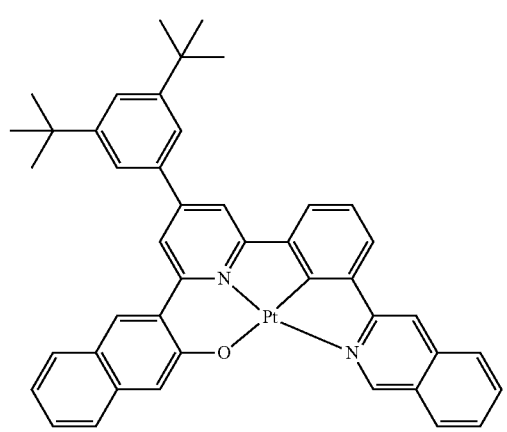
Complex 109
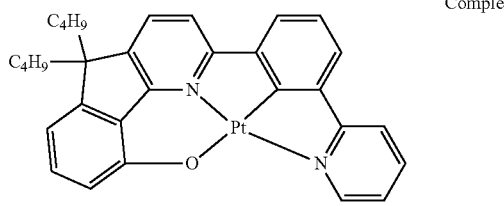
Complex 110
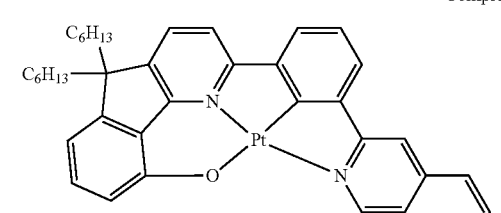
Complex 111
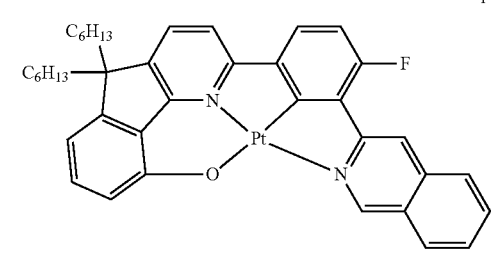
Complex 112
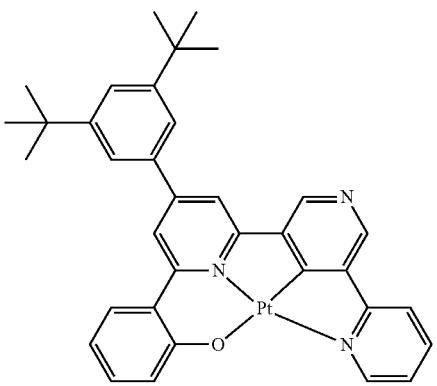
Complex 213
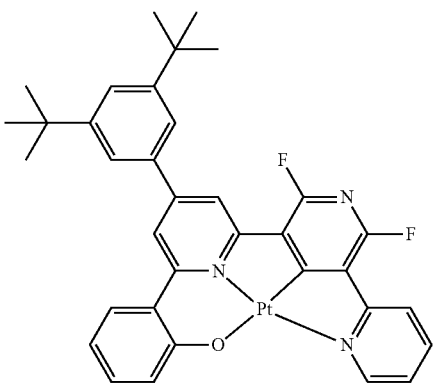
Complex 214
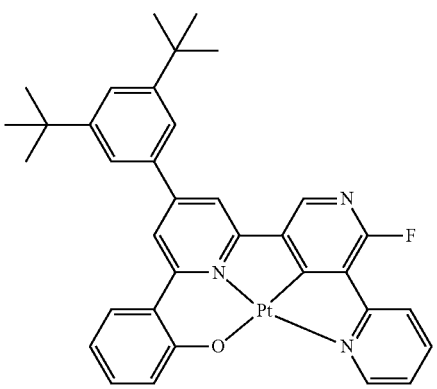
Complex 215
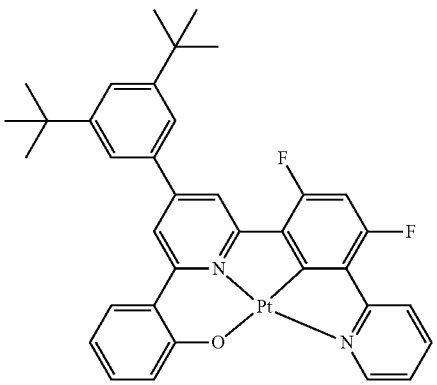

Complex 216
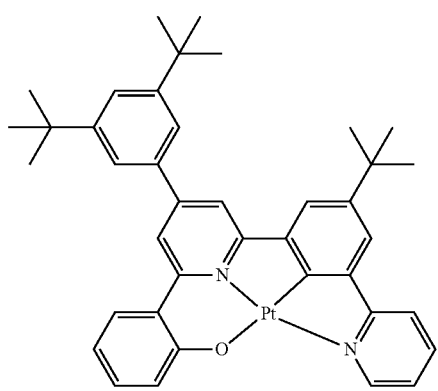
Complex 217
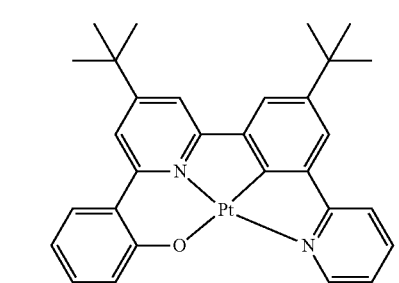
Complex 218
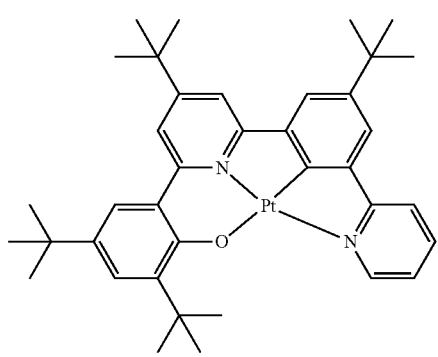
Complex 219
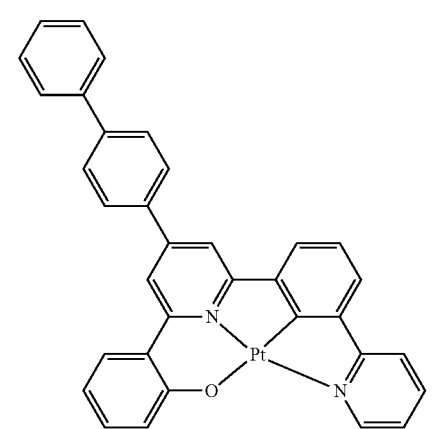
Complex 220
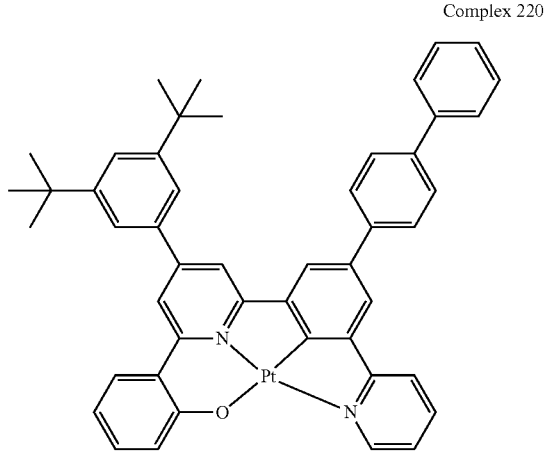
Complex 221
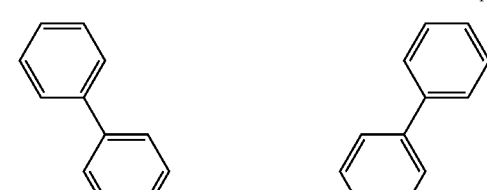
Complex 222
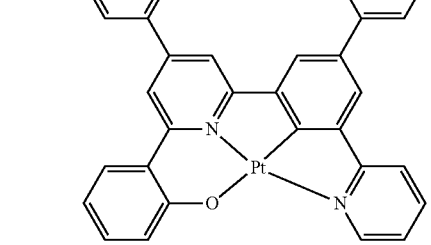
Complex 223
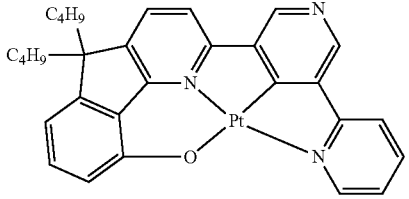
Complex 224
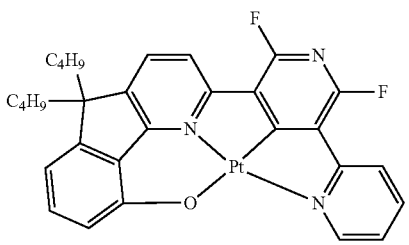
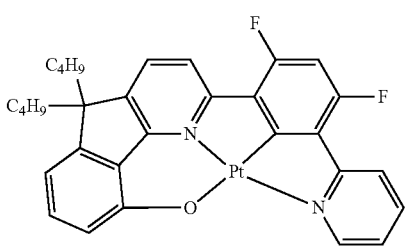

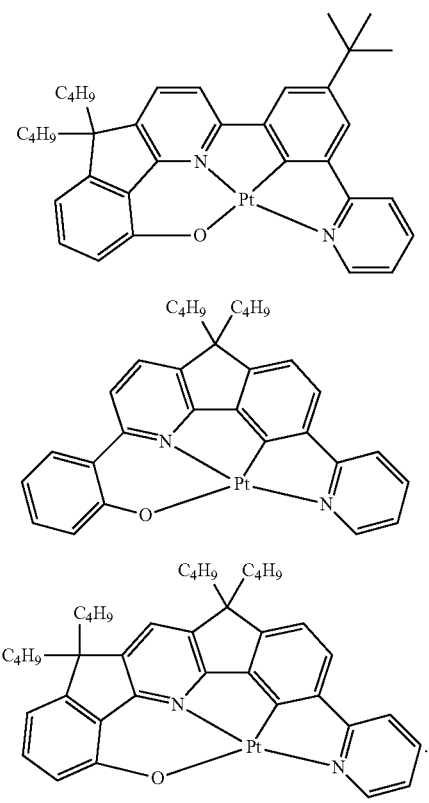

Complex 225

Complex 226

Complex 227

3. An organic light-emitting diode (OLED) comprising one or more organometallic complex described in claim 1 as a light-emitting material(s).

4. A polymer light-emitting diode (PLED) containing one or more organometallic complex described in claim 1 as a light-emitting material(s).

5. An OLED of claim 3, wherein the OLED is fabricated by thermal deposition.

6. An OLED of claim 3, wherein the OLED is fabricated by spin coating.

7. An OLED of claim 3, wherein the OLED is fabricated by printing.

8. A PLED of claim 4, wherein the PLED is fabricated by spin coating.

9. A PLED of claim 4, wherein the PLED is fabricated by printing.

10. An OLED of claim 5, wherein the OLED emits a single color emission originating from the organometallic complex.

11. A PLED of claim 8, wherein the PLED emits a single color emission originating from the organometallic complex.

12. An OLED of claim 5, wherein the OLED emits a green color with the x-coordinate of CIE≤0.31 and y-coordinate of the CIE≥0.59.

13. A PLED of claim 8, wherein the PLED emits a green color with the x-coordinate of CIE≤0.31 and y-coordinate of the CIE≥0.59.

14. An OLED of claim 5, wherein the OLED emits white emission wherein the emission components come from the organometallic complex.

15. An OLED of claim 5, wherein the OLED emits a white emission which is a combination of emission from the organometallic complex and one or more different emission component(s) from another emitting material(s).

16. A PLED of claim 8, wherein the PLED emits a white emission which is a combination of emission from the organometallic complex and one or more different emission component(s) from another emitting material(s).

17. A method to prepare the organometallic complex of claim 1, comprising:
    coupling a first aromatic system with a nitrogen containing heterocyclic aromatic system to form an intermediate;
    reacting the intermediate with a second aromatic system to form a ligand; and
    reacting the ligand with a platinum compound to form the organometallic complex of claim 1.

18. The method of claim 17, wherein the second aromatic system comprises a methoxy group and a precursor group for pyridine ring formation.

19. The method of claim 18, further comprising demethylating the ligand before reacting the ligand with the platinum compound.

20. The method of claim 17, wherein the platinum compound is potassium tetrachloroplatinate.

* * * * *